(12) United States Patent
Dasari et al.

(10) Patent No.: US 10,006,922 B2
(45) Date of Patent: Jun. 26, 2018

(54) RAMAN SPECTROSCOPY FOR DETECTION OF GLYCATED ANALYTES

(71) Applicant: Massachusetts Institute of Technology, Cambridge, MA (US)

(72) Inventors: Ramachandra Dasari, Shererville, IN (US); Ishan Barman, Boston, MA (US); Narahara Chari Dingari, Somerville, MA (US); Jeon Woong Kang, Melrose, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 14/367,633

(22) PCT Filed: Dec. 21, 2012

(86) PCT No.: PCT/US2012/071408
§ 371 (c)(1),
(2) Date: Jun. 20, 2014

(87) PCT Pub. No.: WO2013/096856
PCT Pub. Date: Jun. 27, 2013

(65) Prior Publication Data
US 2014/0349337 A1     Nov. 27, 2014

Related U.S. Application Data

(60) Provisional application No. 61/579,391, filed on Dec. 22, 2011.

(51) Int. Cl.
*G01J 3/44* (2006.01)
*G01N 33/72* (2006.01)
(Continued)

(52) U.S. Cl.
CPC .......... *G01N 33/723* (2013.01); *G01N 21/65* (2013.01); *G01N 33/49* (2013.01); *G01N 33/726* (2013.01);
(Continued)

(58) Field of Classification Search
CPC .... G01N 21/65; G01N 21/651; G01N 21/658; G01N 2021/656; G01N 3/726;
(Continued)

(56) References Cited

U.S. PATENT DOCUMENTS 5,242,803 A * 9/1993 Burtis ............... B01L 3/502753
                                                                                              422/72
5,553,616 A      9/1996 Ham et al.
(Continued)

FOREIGN PATENT DOCUMENTS

WO      2008/029162 A1     3/2008

OTHER PUBLICATIONS

Bachorik et al., National Cholesterol Education Program recommendations for measurement of low-density lipoprotein cholesterol: executive summary. The National Cholesterol Education Program Working Group on Lipoprotein Measurement. Clin Chem. Oct. 1995;41(10):1414-20.
(Continued)

*Primary Examiner* — Abdullahi Nur
(74) *Attorney, Agent, or Firm* — McCarter & English, LLP; Thomas O. Hoover

(57) ABSTRACT

The present invention relates to the optical measurement of blood analytes, such as glycated hemoglobin (HbA1c) and serum albumin as a functional metric of mean blood glucose in the diagnosis of diabetic patients. Non-enhanced Raman spectroscopy is employed as the analytical method for quantitative detection of blood analytes. Using processing techniques, non-enzymatic glycosylation (glycation) of the
(Continued)

analytes results in measurable and highly reproducible changes in the acquired spectral data, which enable the accurate measurements and classification of glycated and unglycated analytes.

39 Claims, 17 Drawing Sheets

(51) Int. Cl.
*G01N 21/65* (2006.01)
*G01N 33/49* (2006.01)

(52) U.S. Cl.
CPC ... *G01N 2440/38* (2013.01); *G01N 2800/042* (2013.01)

(58) Field of Classification Search
CPC ...... G01N 33/76; G01N 33/723; G01N 33/49; G01J 3/02; G01J 3/44
USPC .............................................. 356/301, 72–73
See application file for complete search history.

(56) References Cited

U.S. PATENT DOCUMENTS

| | | | |
|---|---|---|---|
| 7,139,598 B2 | 11/2006 | Hull et al. | |
| 7,330,746 B2 | 2/2008 | Demuth et al. | |
| 7,518,710 B2* | 4/2009 | Gao | G01N 15/1463 250/461.1 |
| 7,672,702 B2 | 3/2010 | Hwang et al. | |
| 7,725,144 B2 | 5/2010 | Ediger et al. | |
| 7,808,633 B2 | 10/2010 | Maier et al. | |
| 7,990,533 B2 | 8/2011 | Maier et al. | |
| 8,013,991 B2 | 9/2011 | Maier et al. | |
| 8,355,767 B2 | 1/2013 | Hunter et al. | |
| 8,743,358 B2 | 6/2014 | Treado et al. | |
| 9,052,290 B2 | 6/2015 | Treado et al. | |
| 9,157,800 B2 | 10/2015 | Priore et al. | |
| 9,274,046 B2 | 3/2016 | Stewart et al. | |
| 9,329,086 B2 | 5/2016 | Treado et al. | |
| 9,658,104 B2 | 5/2017 | Treado et al. | |
| 9,662,047 B2 | 5/2017 | Barman et al. | |
| 2003/0162242 A1 | 8/2003 | Yonehara | |
| 2006/0211928 A1 | 9/2006 | Hull et al. | |
| 2007/0048746 A1* | 3/2007 | Su | B82Y 15/00 435/6.11 |
| 2007/0060806 A1 | 3/2007 | Hunter et al. | |
| 2007/0076208 A1* | 4/2007 | Koo | G01J 3/44 356/451 |
| 2007/0243634 A1 | 10/2007 | Pamula et al. | |
| 2007/0265532 A1 | 11/2007 | Maynard et al. | |
| 2008/0228050 A1 | 9/2008 | Hwang et al. | |
| 2010/0105020 A1* | 4/2010 | Schmidt | G01N 21/658 435/2 |
| 2012/0035442 A1 | 2/2012 | Barman et al. | |
| 2012/0302892 A1 | 11/2012 | Lue et al. | |
| 2013/0082180 A1 | 4/2013 | Priore et al. | |
| 2013/0114070 A1 | 5/2013 | Gardner, Jr. et al. | |
| 2013/0135609 A1 | 5/2013 | Gardner, Jr. et al. | |
| 2013/0201469 A1* | 8/2013 | Treado | G01N 21/65 356/39 |
| 2013/0208985 A1 | 8/2013 | Beckstead et al. | |
| 2013/0214162 A1 | 8/2013 | Treado et al. | |
| 2013/0218480 A1 | 8/2013 | Fuhrman et al. | |
| 2013/0268204 A1 | 10/2013 | Maier | |
| 2013/0321813 A1 | 12/2013 | Treado et al. | |
| 2013/0327129 A1* | 12/2013 | Jung | G01N 30/74 73/61.55 |
| 2013/0342683 A1 | 12/2013 | Nelson et al. | |
| 2014/0016116 A1 | 1/2014 | Maier et al. | |
| 2014/0042322 A1 | 2/2014 | Treado et al. | |
| 2014/0043488 A1 | 2/2014 | Treado et al. | |
| 2014/0093147 A1 | 4/2014 | Stewart et al. | |
| 2014/0104607 A1 | 4/2014 | Treado et al. | |
| 2014/0118722 A1 | 5/2014 | Treado et al. | |
| 2014/0198315 A1 | 7/2014 | Priore et al. | |
| 2014/0231626 A1 | 8/2014 | Nelson et al. | |
| 2014/0267684 A1 | 9/2014 | Nelson et al. | |
| 2014/0268104 A1 | 9/2014 | Treado et al. | |
| 2015/0294076 A1 | 10/2015 | Treado et al. | |
| 2016/0100777 A1 | 4/2016 | Bechtel et al. | |
| 2017/0146403 A1 | 5/2017 | Nelson et al. | |
| 2017/0202462 A1 | 7/2017 | Motz et al. | |
| 2017/0281059 A9 | 10/2017 | Bechtel et al. | |

OTHER PUBLICATIONS

Barman et al., Accurate spectroscopic calibration for noninvasive glucose monitoring by modeling the physiological glucose dynamics. Anal Chem. Jul. 15, 2010;82(14):6104-14.

Barman et al., Raman spectroscopy-based sensitive and specific detection of glycated hemoglobin. Anal Chem. Mar. 6, 2012;84(5):2474-82.

Berger et al., Feasibility of measuring blood glucose concentration by near-infrared Raman spectroscopy. Spectrochim Acta A Mol Biomol Spectrosc. Feb. 1997;53A(2):287-92.

Berger et al., Multicomponent blood analysis by near-infrared Raman spectroscopy. Appl Opt. May 1, 1999;38 (13):2916-26.

Buschman et al., Raman microspectroscopy of human coronary atherosclerosis: biochemical assessment of cellular and extracellular morphologic structures in situ. Cardiovasc Pathol. Mar.-Apr. 2001;10(2):69-82.

Cohen et al., Red cell life span heterogeneity in hematologically normal people is sufficient to alter HbA1c. Blood. Nov. 15, 2008;112(10):4284-91.

Dingari et al., Investigation of the specificity of Raman spectroscopy in non-invasive blood glucose measurements. Anal Bioanal Chem. Jul. 2011;400(9):2871-80.

Dingari et al., Raman spectroscopy provides a powerful diagnostic tool for accurate determination of albumin glycation. PLoS One. 2012;7(2):e32406. 11 pages.

Dou et al., Quantitative analysis of metabolites in urine using a highly precise, compact near-infrared Raman spectrometer. Vibrational Spectroscopy. Dec. 1996;13(1):83-89.

Filik et al., Drop coating deposition Raman spectroscopy of protein mixtures. Analyst. Jun. 2007;132(6):544-50.

Hanlon et al., Prospects for in vivo Raman spectroscopy. Phys Med Biol. Feb. 2000;45(2):R1-59.

Hicks, SERS, Surface Enhanced Raman Spectroscopy. MSU CEM 924. 9 pages (2001).

Ibrahim et al., Analysis of the structure and vibrational spectra of glucose and fructose. Eclectica Quimica. 2006;31 (3):15-21.

Kang et al., Combined confocal Raman and quantitative phase microscopy system for biomedical diagnosis. Biomed Opt Express. Sep. 1, 2011;2(9):2484-92.

Kiran et al., Selective detection of HbA1c using surface enhanced resonance Raman spectroscopy. Anal Chem. Feb. 15, 2010;82(4):1342-8.

Kopecky et al., Drop Coating Deposition Raman—A New Method in Raman Spectroscopy for Biomolecular Samples of Low Concentrations. Retrieved online at: http://www.xray.cz/setkani/abst2005/kopecky.htm. 1 page. Mar. 2005.

Manoharan et al., Histochemical analysis of biological tissues using Raman spectroscopy. Spectrochimica Acta Part A: Molecular and Biomolecular Spectroscopy. Feb. 1996;52(2):215-249.

McMurdy et al., Raman spectroscopy-based creatinine measurement in urine samples from a multipatient population. Appl Spectrosc. May 2003;57(5):522-5.

Movasaghi et al., Raman Spectroscopy of Biological Tissues. Applied Spectroscopy Reviews. Sep. 2007;42 (5):493-541.

Ortiz et al., Validation of the drop coating deposition Raman method for protein analysis. Anal Biochem. Jun. 15, 2006;353(2):157-66.

Ovchinnikov et al., Surface-Enhanced Raman Scattering (SERS). Slideshow presentation. International conference on Quantum Nano-Bio, and Micro Technologies. ICQNM, 80 pages, Aug. 19, 2012.

(56) References Cited

OTHER PUBLICATIONS

Pandey et al., Emerging trends in optical sensing of glycemic markers for diabetes monitoring. Trends Analyt Chem. Jan. 1, 2015;64:100-108.
Park et al., Selective electrochemical sensing of glycated hemoglobin (HbA1c) on thiophene-3-boronic acid self-assembled monolayer covered gold electrodes. Anal Chem. Nov. 1, 2008;80(21):8035-44.
Pichardo-Molina et al., Raman spectroscopy and multivariate analysis of serum samples from breast cancer patients. Lasers Med Sci. Nov. 2007;22(4):229-36.
Rohleder et al., Comparison of mid-infrared and Raman spectroscopy in the quantitative analysis of serum. J Biomed Opt. May-Jun. 2005;10(3):031108. 10 pages.
Shao et al., In vivo blood glucose quantification using Raman spectroscopy. PLoS One. Oct. 25, 2012;7(10):e48127. 6 pages.
Silveira et al., Quantifying glucose and lipid components in human serum by Raman spectroscopy and multivariate statistics. Lasers Med Sci. May 2017;32(4):787-795.
Zhang et al., Chemical segregation and reduction of Raman background interference using drop coating deposition. Appl Spectrosc. Aug. 2004;58(8):929-33.
Zhang et al., Raman detection of proteomic analytes. Anal Chem. Nov. 1, 2003;75(21):5703-9.

\* cited by examiner

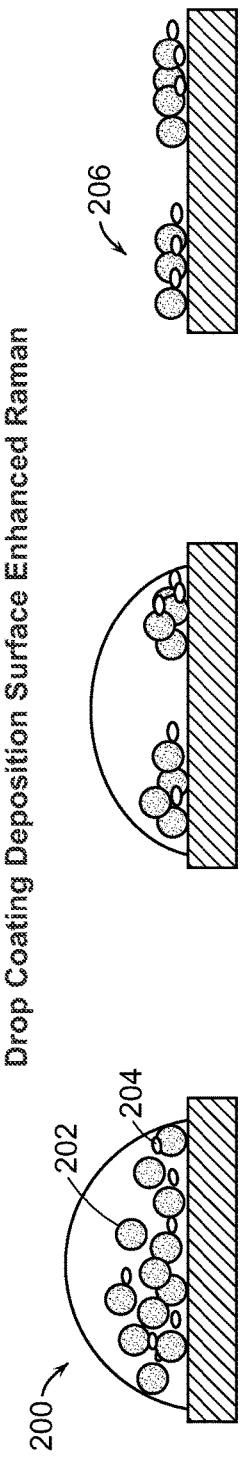
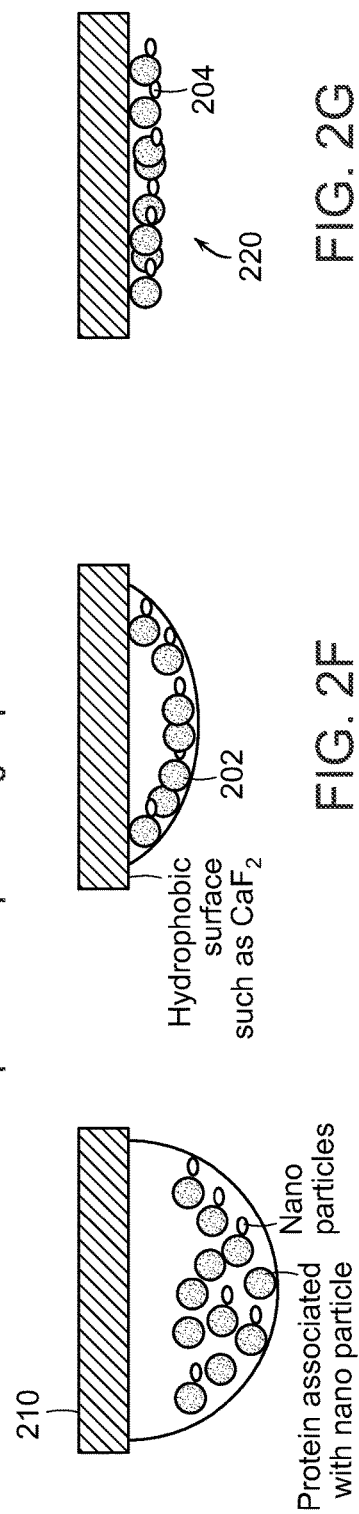

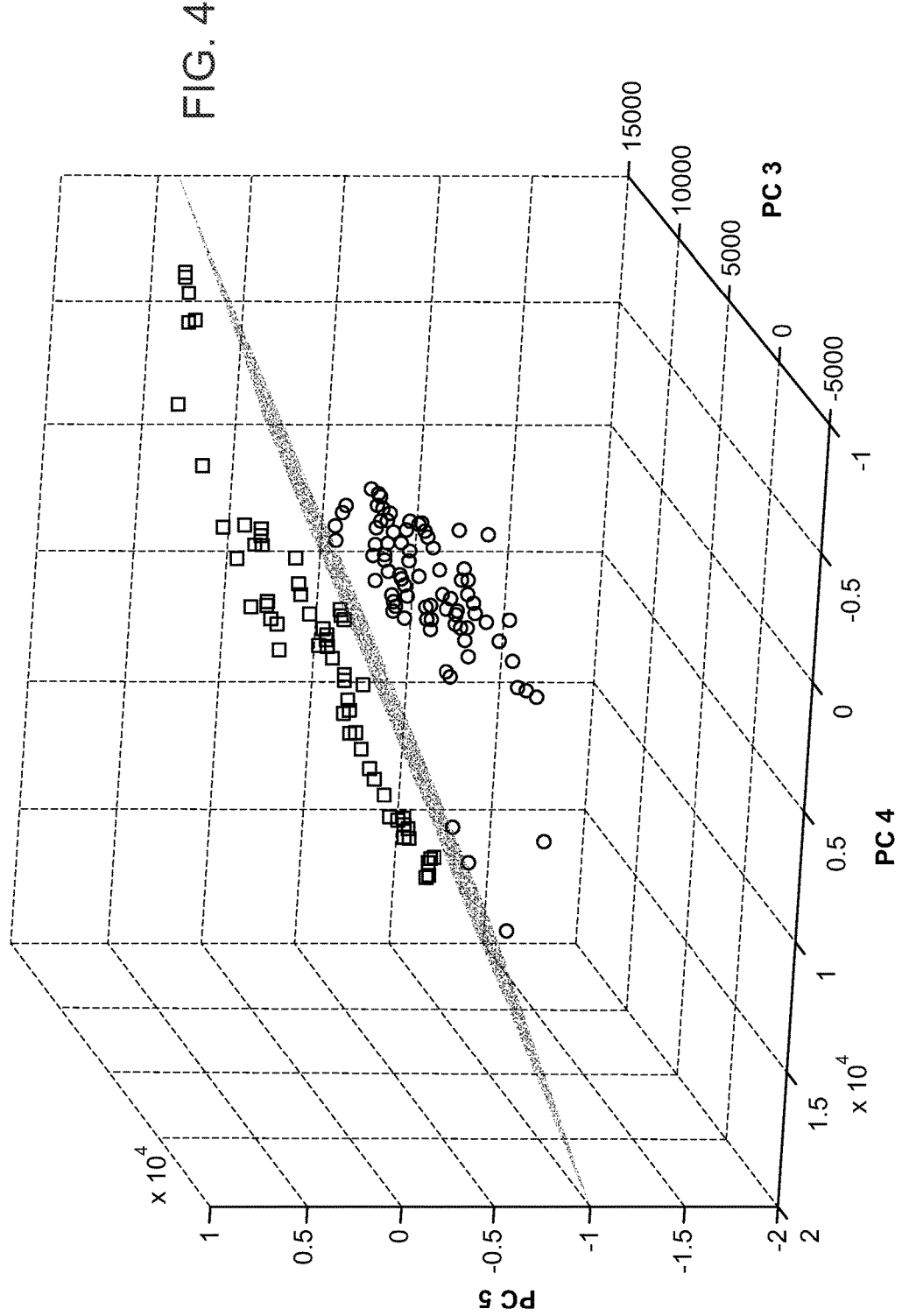

RAMAN SPECTROSCOPY FOR DETECTION OF GLYCATED ANALYTES

CROSS REFERENCE TO RELATED APPLICATIONS

This application is a 35 U.S.C. § 371 national stage filing of International Application No. PCT/US2012/071408, filed on Dec. 21, 2012, which claims the priority to U.S. Provisional Application No. 61/579,391, filed on Dec. 22, 2011, the entire contents of which are being incorporated herein by reference.

STATEMENT REGARDING FEDERALLY SPONSORED RESEARCH OR DEVELOPMENT

This invention was made with government support under Grant No. P41-RR02594 awarded by the NIH National Center for Research Resources. The government has certain rights in this invention.

BACKGROUND OF THE INVENTION

Glucose forms the most ubiquitous energy source in biology. In humans, glucose is primarily derived from the breakdown of carbohydrates in the diet or in body stores (glycogen), in addition to secondary endogenous synthesis from protein or from the glycerol moiety of triglycerides. Importantly, even under diverse conditions (such as feeding, fasting and severe exercise), the blood glucose level is maintained within a fairly narrow interval, 70-120 mg/dL, by the body's homeostatic system. For an average person, this implies that the total quantity of glucose in the blood and body fluids is approximately 5 grams—a remarkably small number given the typical carbohydrate intake per day. To maintain this natural balance, an intricate set of biomolecule interactions, modulated by glucoregulatory hormones such as insulin, needs to occur. However, in people afflicted with diabetes mellitus, the defective nature of carbohydrate metabolism (stemming from inadequate insulin production, response or both) leads to the presence of high blood glucose.

Diabetes mellitus, characterized by the defective regulation of blood glucose, is the most common disorder of the endocrine system affecting nearly 24 million people in the US alone. Given the lack of suitable therapeutic options, effective glycemic control is imperative in avoiding acute and chronic complications, such as diabetic coma, and microvascular and macrovascular complications. To this end, the development of a non-invasive blood glucose sensor is pursued using a variety of optical and spectroscopic modalities. While monitoring blood glucose remains the gold standard for continuous monitoring and evaluation of treatment options, glycated hemoglobin (HbA1c) has gained approval in the medical community in assessing the long-term history of glycemic control. HbA1c is formed by the non-enzymatic glycosylation (glycation) of hemoglobin exposed to blood glucose and therefore has a strong correlation with the average glucose concentrations in the bloodstream in the preceding three month period (life span of the erythrocytes). Due to this strong correlation, HbA1c levels have been regularly used for monitoring long-term glucose control in established diabetics and has been recently approved for screening for diabetes (HbA1c≥6.5%) and pre-diabetes (5.7%≤HbA1c≤6.4%) in the United States.

Presently, HbA1c is distinguished from non-glycated hemoglobin using assay techniques such as high-performance liquid chromatography (HPLC), isoelectric focusing and immunoassay. However, the presence of hemoglobin variants and other clinical factors such as uremia may interfere with HbA1c determinations. As an alternate method for HbA1c detection, others have recently reported the application of surface enhanced resonance Raman spectroscopy (SERRS). Though promising in approach, precise quantification of the analyte of interest (HbA1c) using SERSS is difficult due to poor spectral reproducibility and generation of spurious background signals.

SUMMARY OF THE INVENTION

The present invention relates to the optical measurement of blood analytes that are indicative of the glycemic history of diabetics, such as glycated hemoglobin and glycated albumin. A preferred embodiment uses Raman measurement of a blood sample obtained from a patient to determine analyte concentration. Samples can be processed using drop coating deposition Raman (DCDR) spectroscopy for the selective detection of HbA1c. Previously, pioneering studies by Ben-Amotz and co-workers have shown that DCDR provides significant signal amplification by pre-concentration of the analytes of interest, especially proteins. In DCDR, spectra are acquired from the ring pattern of analytes deposited from a drying drop, which is a formed as a result of the interplay of contact line pinning, solvent evaporation and capillary flow. The coffee ring pattern results in significant constituent pre-concentration that provides strong and reproducible Raman signals for different bio-analytes without considerable loss of their solution conformation. A preferred embodiment of the invention can use a suspended sample that can be positioned, for example, on an inverted hydrophobic surface and dried so as to concentrate the sample for measurement.

Another preferred embodiment provides for multimodal imaging in conjunction with Raman spectral measurements of samples such as the concentrated samples as described herein. The system provides for the forming of bright field images, quantitative phase images and confocal images that can be used to identify morphological structures within the field of view and enable the formation of Raman images of specific features within the field of view. The system can allow selection of a region of interest within the field of view for more detailed spectral imaging and analysis.

Glycation of hemoglobin results in changes in the acquired Raman spectra that facilitate the accurate classification of glycated and unglycated (pure) hemoglobin using multivariate techniques. On close examination, the acquired Raman spectra reveal excellent reproducibility of spectral characteristics at different locations in the ring pattern and show a linear response (between the spectral intensity and the analyte concentration). Furthermore, in mixture samples consisting of both analytes, the developed calibration models show a high degree of prediction accuracy even at two orders of magnitude smaller concentrations in comparison to physiological levels. Given the sensitivity, linearity of response and rapidity of measurement, this method functions both as a stand-alone analysis and complements existing standard analytical/diagnostic techniques used for glycemic marker detection. A preferred embodiment uses these methods in combination with other specific vibrational methods, e.g., 2D-IR spectroscopy or surface enhanced Raman spectroscopy. Techniques such as confocal microscopy may also be combined with the Raman spectroscopy of the present invention. To this end, a multimodal microscopy system is provided. Raman spectroscopy may therefore

BRIEF DESCRIPTION OF THE DRAWINGS

FIGS. 2B-2D: Illustrate the formation of a ring sample in accordance with preferred embodiments of the invention.

FIGS. 2E-2G: Illustrate the formation a concentrated sample in accordance with preferred embodiment of the invention.

FIG. 4: Scores plot corresponding to principal components 3, 4 and 5 for the spectral dataset acquired from the single protein Hb and HbA1c drop-coated rings. The Hb and HbA1c samples are indicated by circles and squares, respectively.

DETAILED DESCRIPTION OF THE INVENTION

Figure 1A:
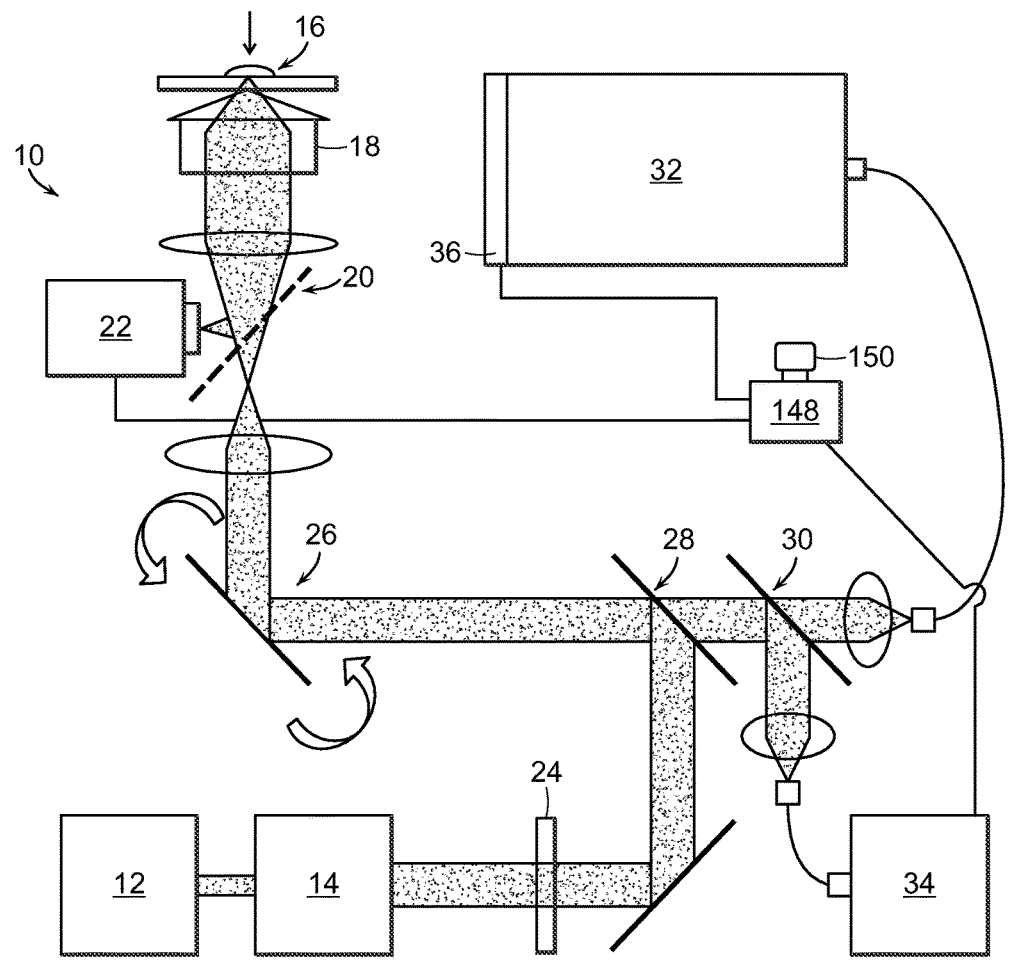
FIG. 1A: A system for Raman-spectral measurement in accordance with the invention.

The present invention provides a method for the detection of one or more glycated analytes in a sample using Raman shifted light. The method can include obtaining a solution of the sample analyte and processing the solution such as by concentrating the sample. Subsequently, the concentrated sample can be illuminated with light and Raman data is acquired from the concentrated sample. The Raman data is then anaylzed to determine levels of glycated analytes.

Said analytes are typically proteins, but can also be peptides, nucleotides, glycans and the like. In a preferred embodiment, the analytes are selected from the group consisting of hemoglobin and serum albumin. In another embodiment the sample is selected from the group consisting of serum and whole blood.

The present invention also provides methods for the simultaneous detection of levels of glycated hemoglobin and serum albumin. In a preferred embodiment, an aliquot of the solution is placed on a surface and air dried. Raman data are then collected using the dried solution. Using principal component analysis, levels of glycated hemoglobin and serum albumin can be determined.

The present invention further includes a method of detecting levels of either glycated hemoglobin or glycated serum albumin. Said method can comprise the steps of obtaining a solution of a whole blood sample including hemoglobin. By separating blood components into serum and cellular components, Raman data can be acquired using a Raman measurement system. Principal component analysis to determine levels of glycated hemoglobin and glycated serum albumin.

The present invention further contemplates a multimodal imaging system, having a plurality of modalities, wherein one modality is a Raman measurement system and a further modality can be an imaging system using confocal reflectance, quantitative phase contrast, 2D infrared and/or bright field microscopy, for example.

The present invention uses a non-enhanced Raman spectroscopy for quantitative measurements of glycated hemoglobin and serum albumin as a route to expanding the range of Raman-based analytical and clinical diagnostic methods. To this end, measurements were undertaken to (1) evaluate the ability to distinguish between glycated and nonglycated samples; (2) quantify the prediction accuracy and precision of these analytes in two-component mixture samples; and (3) investigate the reproducibility of the measurements in mixture samples from the resultant dried ring patterns. Spectroscopic measurements are taken from single protein drop-coated samples, namely those obtained from the aqueous solutions of the analytes under investigation. These measurements are employed to investigate the spectral differences, if any, and the possibility of exploiting these differences for selective fingerprinting of the glycemic marker. In order to accomplish objective (2), two-component mixtures (i.e. mixtures containing both the glycated and nonglycated analytes in different proportions) were studied.

Specifically with respect to hemoglobin, this system represents a hemolysate model, the product resulting from the lysis of erythrocytes, and adds an important layer of complexity to studies in single protein or protein/buffer solutions. Moreover, it provides an ideal platform to study some of the intricacies of spectroscopic measurements prior to analyzing more complex, multi-component mixtures. Finally, for objective (3), 2D spatial Raman mapping was performed on the drop-coated two-component mixture samples.

One embodiment of the invention provides a Raman system 10 shown in FIG. 1A. A frequency-doubled Nd-YAG laser 12 is the pump source for Ti:Sapphire laser 14, which is the excitation source for a confocal Raman system. Sample 16 is disposed above objective lens 18, which may be a water immersion objective lens such as the Olympus UPLSAPO60XWIR 60×/1.20. Flip mirror 20 placed after the objective lens allows the sample image to be observed at CCD 22. Light emitting diodes (LEDs) can be used as a second light source for bright field imaging. The collimated beam from light source 14 is band pass filtered at 24 and redirected to galvanometer mirrors 26 by a first dichroic mirror 28. Both the Raman signal and the confocal reflectance signal passed to a second dichroic mirror 30. The Raman signal is delivered to spectrograph 32 with an integrated imaging detector 36, while the confocal reflectance is delivered to photomultiplier system (tube and controller (PMT)) 34.

Figure 1B:
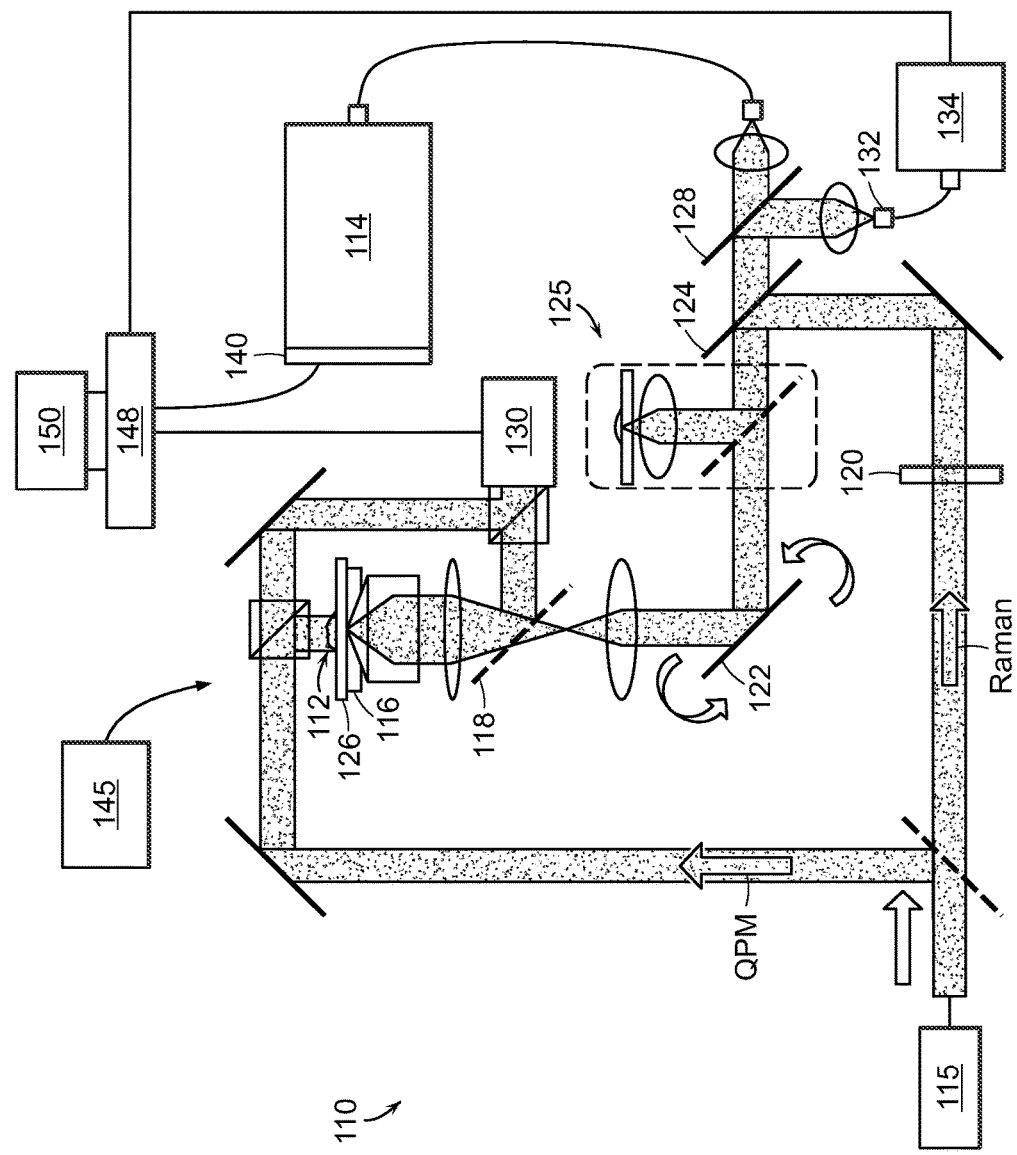
FIG. 1B: Another embodiment of a system for Raman-spectral measurement in accordance with the invention.

According to another embodiment of the invention, a Raman system 110 used for these measurements is shown in FIG. 1B, which illustrates a multimodal microscopy system which can combine four imaging modalities, all of which may be used independently or in combination. A tunable CW Ti:Sapphire laser (3900S, Spectra-Physics) 115 set at an 785 nm excitation wavelength can be used as a light source. The Ti:Sapphire laser is pumped using frequency-doubled Nd:YAG laser (Millennia 5sJ, Spectra-Physics). The Raman back-scattered light from the sample 112 is transmitted by a multimode fiber to a spectrograph 114 (Kaiser Holospec f/1.8i) and an imaging device 140, such as a liquid nitrogen-cooled CCD (LN/CCD 1340/400-EB, Roper Scientific). The laser power was measured at the sample to be ca. 3 mW. A water immersion objective lens 116 (Olympus UPLSAPO60XWIR 60×/1.20) was used to both focus the laser to a spot size of approximately 1 μm at the drop-coated substrate surface and to collect the back-scattered Raman light. Movable mirror 118, placed after lens 116 allows the image focused at the sample plane from the incoherent transmission source to be observed at the video camera with about 67× magnification. The collimated beam is band pass filtered at 120 and redirected to dual-axis galvanometer mirrors 122 by a first dichroic mirror 124. After the galvanometer mirrors, the beam size at the sample is adjusted by a telescope and focused at the sample plane by an objective lens; XY positioning is achieved by a micrometer controlled stage (telescope, lens and stage are collectively 126). Remaining Rayleigh light after the first dichroic mirror is filtered again by a second dichroic mirror 128. An optional measuring stage 125 can be used for Raman measurements not requiring spatial resolution. Camera 130 is used to capture the image. The confocal reflectance signal is delivered to photomultiplier tube 132 and amplified by PMT controller 134. Note that although the pumped Ti:Sapphire laser was used here as a part of a Raman microscope, a simpler laser such as a stabilized diode system can also function as an excitation light source. The detector system components in these embodiments can be connected to a data processor or computer 148 to provide imaging processing and analysis of the spectral data. The spectral data can be stored in memory and displayed using display 150. The computer can be programmed with software programs configured to process the image data and spectral data to determine quantitative characteristics of the sample including the concentration and distribution of selected analytes in the sample as described herein. A sample processing system 145 as further described herein can be used to process the sample.

Further systems and methods for measuring blood glucose and analyzing spectral data are described in U.S. application Ser. No. 13/167,445 filed on Jun. 23, 2011 and International Application PCT/US2011/046750, filed on Aug. 5, 2011, the entire contents of the above referenced applications being incorporated herein by reference. The analysis can utilize non-linear representation of data such as a support vector machine (SVM) to analyze the spectral data as described in the above referenced applications. The systems including those used for transmission or reflection measurements of Raman shifted light from the tissue can be used with the methods described herein.

Figure 1C:
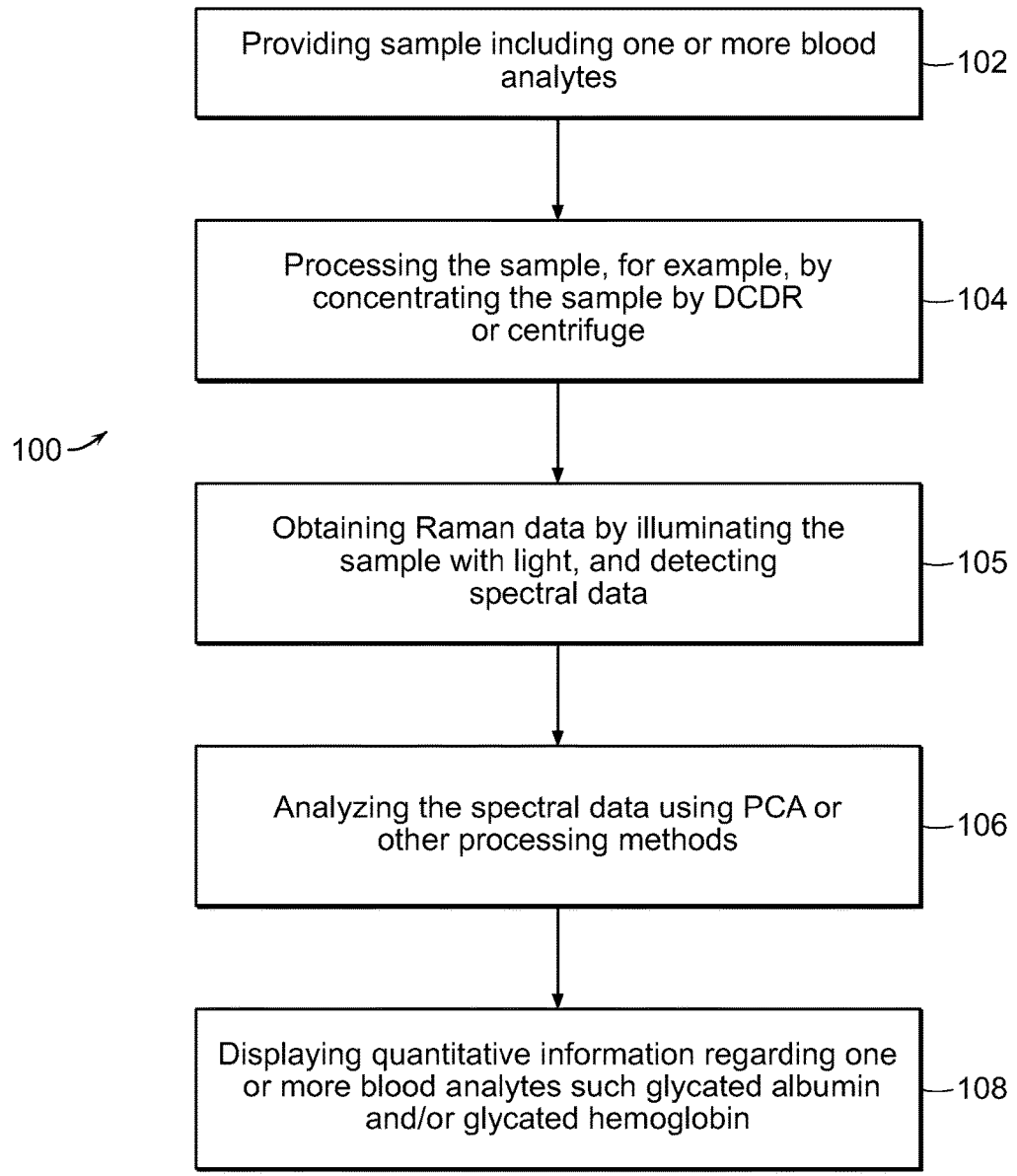
FIG. 1C: Schematically illustrates an embodiment of a process sequence in accordance with the invention.

Illustrated in FIG. 1C is a process sequence 100 for measuring a blood analyte in accordance with preferred embodiments of the invention. After obtaining a blood sample 102, one or more techniques can be used to process 104 the sample, such as, by concentrating the sample. Raman spectra are then obtained 105 and processes 106 using a data processor and displayed 108 using a display. Further details regarding the methods are described herein.

To illustrate this system for evaluating glycated and nonglycated hemoglobin, hemoglobin powder (in lyophilized form) was obtained from Sigma-Aldrich (St. Louis, Mo., USA) and frozen HbA1c liquid from Lee Biosolutions, Inc. (St. Louis, Mo., USA). For the single protein samples, aqueous solutions of hemoglobin were prepared in the range of 10-155 μM (the typical physiological range is between 1.55-2.7 mM or, ca. 10-17.5 g/dL. Similarly, HbA1c samples were formulated with concentrations in the range of 4-34 μM (typical physiological values are between 4 and 25% of the aforementioned hemoglobin values with the critically important range being 5-10%). For all sample preparations, PESTANAL water (34478, Fluka) was used to ensure higher reproducibility of the measurements. For the two-component mixture measurement, 16 total samples were formulated by pipetting different volumes of Hb and HbA1c from their respective stock solutions. The final concentration ranges for Hb and HbA1c in the two-component mixture models were ca. 2-100 μM and 5-25 μM, respectively (with the minimum glycated hemoglobin percentage in these hemolysate models being ca. 5%).

Figure 2A:
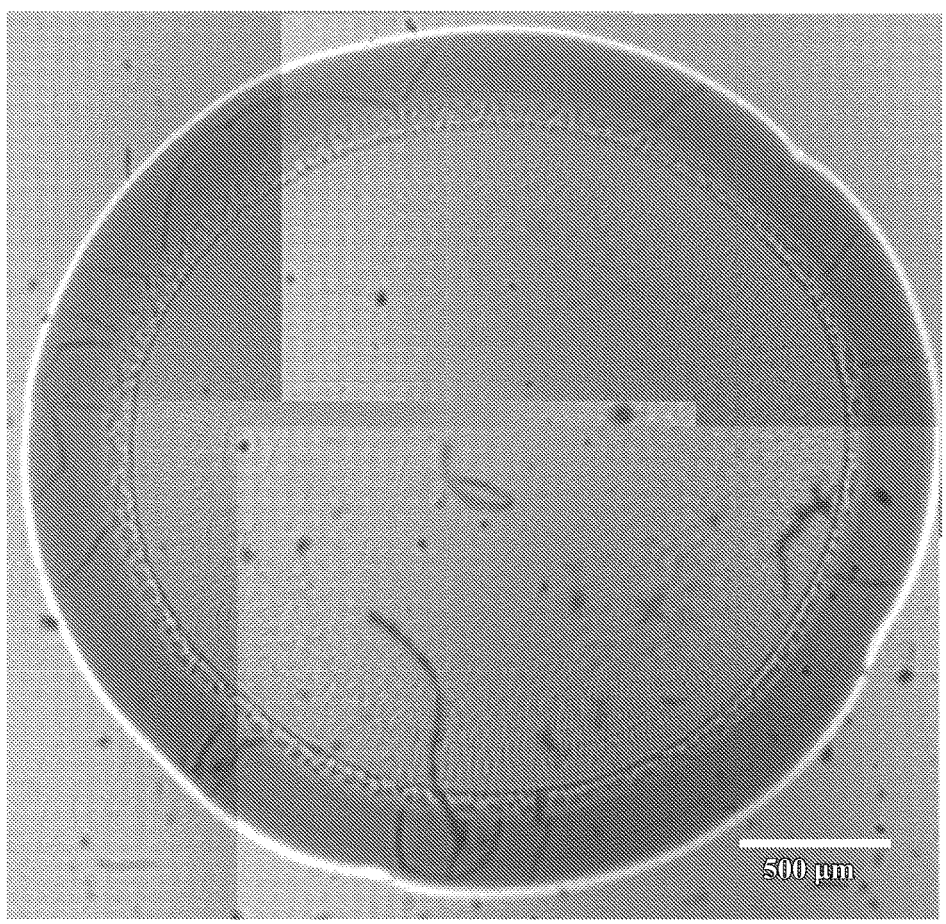
FIG. 2A: Composite photograph showing the drop coating ring pattern produced by air-drying Hb and HbA1c mixture solution on a quartz substrate; the proteins are observed to be concentrated on the ring with little or no material left in the interior region; the ring width is ca. 300 µm and the ring diameter is 3.5 mm.

Prior to Raman spectroscopic measurement, aliquots (4 μL) of these solutions (i.e. the single proteins and the two-component mixtures) was pipetted on to the quartz coverslips and air-dried for approximately 20 minutes under temperature and humidity-controlled laboratory conditions. FIG. 2A shows the ring pattern obtained by air-drying a representative two-component mixture sample. The width of the protein rings produced after solvent evaporation scaled roughly linearly with protein concentration in the range of 50-350 μm. FIGS. 2B-2D show a drying sequence wherein a drop 200 is positioned on a substrate wherein the sample includes proteins 202 that can be associated with nanoparticles 204, in this example. The drops undergo drying that generates a ring pattern (FIG. 2C) that dries into ring 206.

In a further preferred embodiment, an inverted drop coating deposition Raman spectroscopy (iDCDR) system can be utilized. Under certain circumstances, the "coffee-ring" effect can induce uneven distributions of analytes within the dried droplet area. To control the spatial distribution of the colloidal particles in the dried area a sample preparation protocol based on the drying of an inverted ("suspended") sample or droplet can be used. This prevents the problems arising from the clustering of species at the liquid-solid contact of a conventional drying droplet. The evaporation of the solvent in the inverted droplet also helps accumulate the analytes in a single confined area in the droplet region (as opposed to the annular ring).

An inverted droplet from a hydrophobic surface changes the dynamics in the droplet during the drying process. The application of a hydrophobic surface prevents the spread of the droplet and keeps the droplet confined as much as possible.

In the inverted droplet, since the glycated proteins are heavy (in comparison to small molecules in buffer solution and other salts), they tend to accumulate at the (inverted) tip of the droplet due to gravitational force. Analogous to the physical processes taking place in a conventional drying droplet placed on a surface, due to the larger evaporation rate at the solid-liquid contact line and the pinning of the contact line, solvent flow is generated from the center of the droplet towards the edges. This solvent flow tries to drag the accumulated species from the middle of the droplet to the peripheral region. However, this force is not substantive enough to drag the accumulated heavy particles and molecular species at the tip of the inverted droplet.

Thus, only the small molecules tend to migrate to the edges. In contrast, the heavier glycemic markers, which are accumulated at the tip of the inverted droplet, do not migrate with the outward flow but rather adhere to the central confined area of the substrate surface as the solvent volume diminishes.

This embodiment provides a more consistent distribution of the analyte molecules and is more conducive to clinical measurements where the focal spot of the laser beam does not need to be positioned on the annular ring.

FIGS. 2E-2G show a conjugation with (Ag/Au) nanoparticles 204, which can further enhance the sensitivity of the Raman signal via the surface-enhanced effect (excitation of localized surface plasmons). A hydrophobic surface on substrate 210 can be used so that during drying the proteins 202 and nanoparticles form a concentrate sample 220.

Spectra were acquired with a 20 second acquisition time, or less, from the approximate geometric center of the deposited rings. For the quantification analysis, multiple spectra were collected from each point (5 spectra per point) and multiple such points (3 points per sample at uniform separation in the direction of the arc of the ring) were probed to ascertain the measurement precision. The coverslips used were all made of quartz in order to avoid the strong fluorescence of glass. For the 2D spatial Raman mapping, a total of 121 spectra were collected over a 44×44 μm field of view with inter-point distance of 4 μm.

The acquired Raman spectra were subject to processing, such as vertical binning and cosmic ray removal prior to further data analysis (no background fluorescence removal was undertaken). It is worth noting that the spectra of the bare substrate and that obtained from the center of the drop-coated deposit (not to be confused with the center of the ring) were essentially identical and did not exhibit characteristic Raman features of any of the sample components. Consequently, further references to the (drop-coated) ring indicate that the annular ring is where the analyte(s) are concentrated, unless otherwise noted. Also, laser power-dependent studies display no evidence for optical and/or thermal damage of either the analytes or substrates used in this study. Indeed, the power at the sample plane was intentionally kept at low levels to ensure no thermal/photochemical damage to the drop-coated protein rings.

To evaluate the method in regard to specific discrimination between unglycated and glycated hemoglobin samples, principal component analysis (PCA) was employed on the entire spectral dataset acquired from single protein samples using the Statistics Toolbox of MATLAB R2010b (Math Works, Natick, Mass.). Specifically, the entire dataset was constituted by 75 and 60 spectra acquired from 5 and 4 separate Hb and HbA1c samples at different concentrations, respectively. As noted above, 15 spectra were acquired per sample with 5 measurements each at different points in the protein ring to test its homogeneity (or lack thereof). PCA is a powerful tool for exploratory data analysis and the linear multivariate PCA models are developed using orthogonal basis vectors (principal components, PC) thereby reducing the high-dimensional spectral data onto a lower dimensional space.

Moreover, in order to characterize the capability of DCDR to provide quantitative measurements of these bioanalytes in hemolysate model systems, partial least squares (PLS) regression was employed. For the hemolysate model systems, 240 spectra acquired from a total of 16 samples were used for data analysis. Due to the relatively limited number of distinct samples, a leave-one-sample-out cross-validation routine was performed to test the predictive power of the data. In the leave-one-sample-out cross-validation employed here, one sample (i.e. 15 spectra) is left out at a time from the calibration data set and the developed model is used to compute the concentration associated with the spectra of the left out sample. This calibration procedure is repeated until all samples have been left out in turn. In particular, for each prediction step, the calibration step for the hemolysate models was based on 225 spectra.

The root-mean-square error of cross-validation (RMSECV) (i.e. square root of the average of the squares of the differences between predicted and reference concentrations) was computed to assess the prediction accuracy of the models. Moreover, the prediction precision was separately calculated as the ratio of the standard deviation obtained at a specific reference concentration to the reference concentration itself. Finally, the relative predictive determinant (RPD) metric was also evaluated to classify and appropriately compare the overall prediction quality of the individual calibration models for the two components, which displayed very different concentration ranges. RPD is defined as the ratio of the standard deviation of the reference concentration in the sample population ($\sigma R$) to the standard error of prediction (the standard deviation & differences between predicted and reference values) ($\sigma_{R-P}$):

$$RPD = \frac{\sigma_R}{\sigma_{R-P}} \quad (1)$$

Figure 3A:
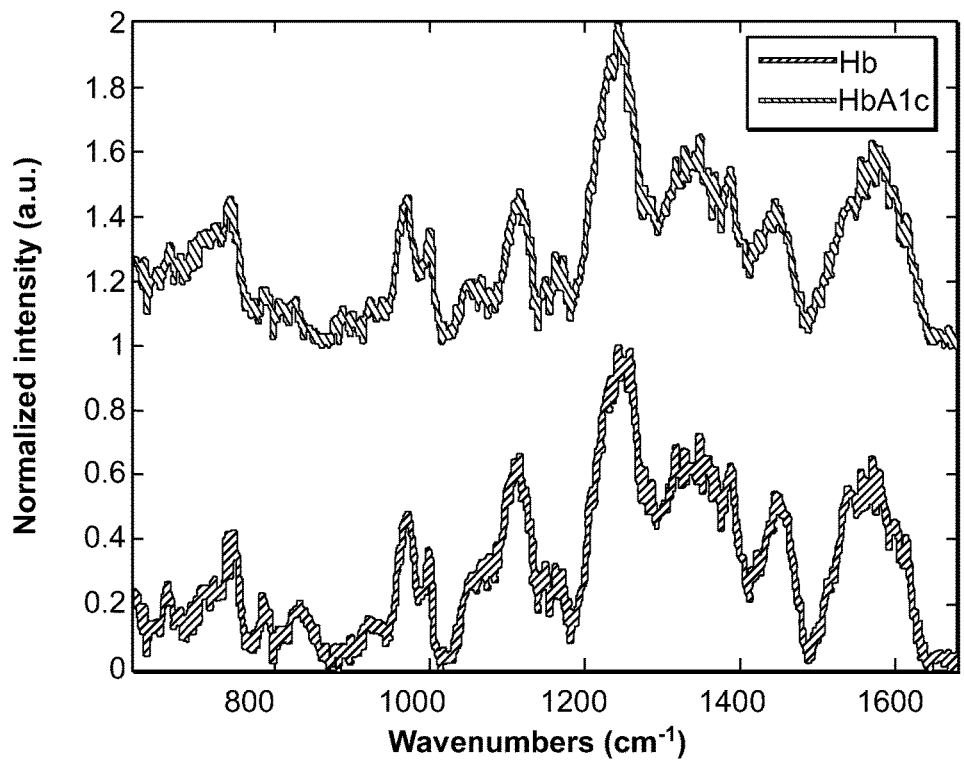
FIG. 3A: Representative Raman spectra acquired from the drop-coated single protein Hb and HbA1c samples derived from ca. 39 µM and 34 µM solutions, respectively (the spectra are normalized and offset for the sake of clarity).

FIG. 3A shows representative spectra acquired from the drop-coated single protein Hb and HbA1c samples derived from ca. 39 µM and 34 µM solutions, respectively (the spectra are normalized and offset for the sake of clarity). The spectra shown in this figure were obtained by averaging 5 spectra obtained from each of these samples. Not unexpectedly, no detectable signal was recorded from the corresponding aqueous Hb and HbA1c solutions. Nevertheless, the acquired DCDR spectra were more representative of the protein in solution form (when concentrated to several mM range) than that obtained from the pure protein powder (i.e. sample bought from the manufacturer). While the two spectra grossly appear to have similar profiles, careful visual inspections exhibit subtle but discernible and highly reproducible spectral shape differences.

Figure 3B:
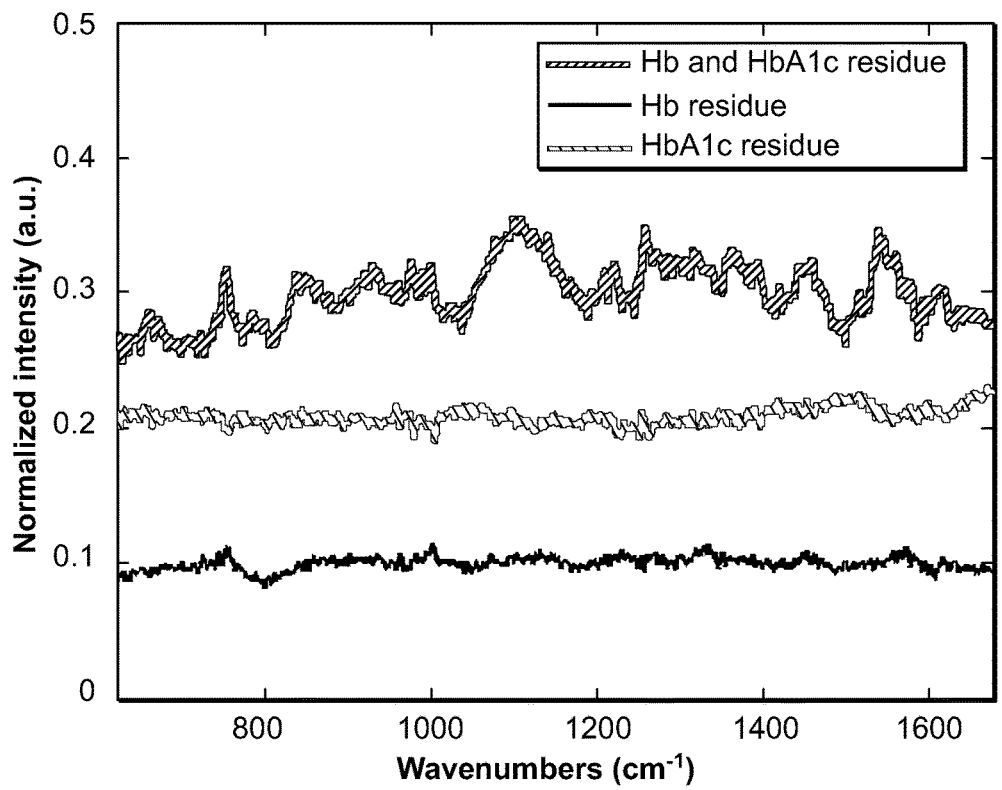
FIG. 3B: Residual plots computed from the difference between: normalized Hb (39 µM) and HbA1c (34 µM) spectra shown in FIG. 3A (red*); normalized Hb spectra from drop-coated rings derived from 39 µM and 19.5 µM (green); normalized HbA1c spectra from drop-coated rings derived from 34 µM and 17 µM (black).

To understand these differences that are embedded in the spectra in a more explicit manner, the residuals were plotted in FIG. 3B. Here, the residuals were obtained from computing the difference between the normalized Hb and HbA1c spectra (FIG. 3A) (red) as well as those obtained from the difference between normalized Hb spectra at 39 µM and 19.5 µM (green) and normalized HbA1c spectra at 34 µM and 17 µM (black). The lack of spectral features in the residuals from the latter two (green and black plots) reveal the highly reproducible nature of the measurements (and the deposits) obtained from the same analyte. Importantly, the presence of subtle but distinct features in the residual plot between Hb and HbA1c deposits highlight the sensitivity of the proposed approach to very small structural variations in the protein molecules. (Identical features were obtained in the residuals calculated from the differences between sample spectra recorded from other concentrations of Hb and HbA1c deposits.) Note that these spectral features do not show a direct correspondence with those acquired from glucose deposits (which expectedly resemble the features obtained from a saturated glucose solution). The variations in the two protein spectra can then be attributed to structural changes in hemoglobin molecule related to the binding of a glucose moiety. Such glycation-induced changes to the hemoglobin molecule can decrease the α-helix content and weaken the heme-globin interaction.

These measurements are consistent with previous measurements of the preservation of protein structure between the solution form and the drop-coated deposits. Indeed, the maintenance of the secondary structure of such deposits have been verified using circular dichroism (CD) spectroscopy and by FITR measurements. Notably, NIR excitation coupled with measurements from the DCDR deposits (in contrast to pure protein powder measurements) substantially reduces the presence of any fluorescence background. This enables the application of multivariate chemometric methods without necessitating the incorporation of background removal procedures and without having to address the enhancement of the noise floor from the presence of a large fluorescence background.

To further establish the ability of the proposed approach in selectively detecting the glycemic marker (HbA1c), multivariate classification was performed on DCDR spectra acquired from the Hb and HbA1c deposits. FIG. 4 shows the scores plot for the DCDR spectra dataset corresponding to principal components 3, 4 and 5. As PCA seeks to explain the net variance in the dataset, the first two PCs in this case (which are largely representative of the background) do not provide the maximum discriminatory power between the 2 classes. However, as evident from the figure, PCs 3-5 provide the capability of distinguishing spectra derived from the above analytes with a remarkable 100% accuracy. It is notable that simple unsupervised exploratory classification can provide this level of discrimination. This re-emphasizes the clear reproducible differences obtained for the spectra of each analyte such that the PCA model is not faulty even at substantially different concentration levels and by potential sample-to-sample variations (stemming largely from imprecision in preparation and measurements). Taken together, FIGS. 3 3A, 3B and 4 establish the ability to successfully distinguish between the two considered analytes, namely Hb and HbA1c. Preferred embodiments are applied to complex system involving numerous other proteins, especially as the concentration levels of Hb and HbA1c are significantly greater relative to other proteins in blood minimizing any potential interference from such components.

Given the performance of PCA in discriminating the analytes from the spectra, partial least squares (PLS) regression was employed to demonstrate the predictive power of the above method. Specifically, this was performed on the hemolysate model systems to assess the prediction accuracy and precision of the proposed approach. For the PLS regression analysis, the number of loading vectors which give the minimum RMSECV was determined in the range of 3-15. Subsequently, to minimize any possibility of overfitting (i.e. inclusion of spurious correlations and noise components), the calibration model corresponding to the minimum number of loading vectors, which provides a less than 5% deviation from the minimum RMSECV, was selected.

Figure 5A:
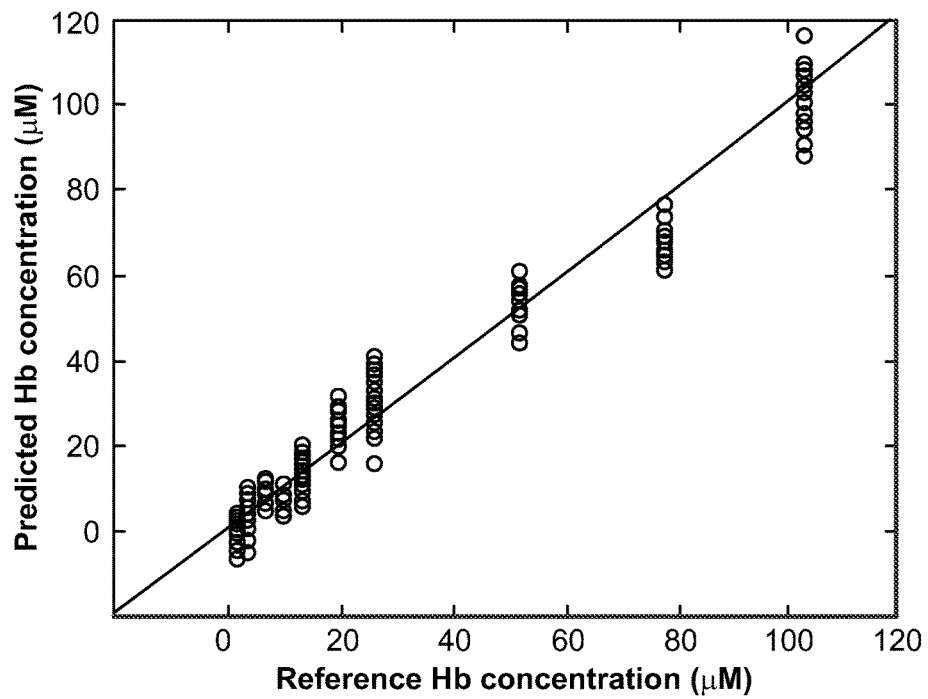
FIGS. 5A and 5B: Prediction results obtained from partial least squares (PLS) regression on the hemolysate model samples: (A) Hb predictions; (B) HbA1c predictions.
Figure 5B:
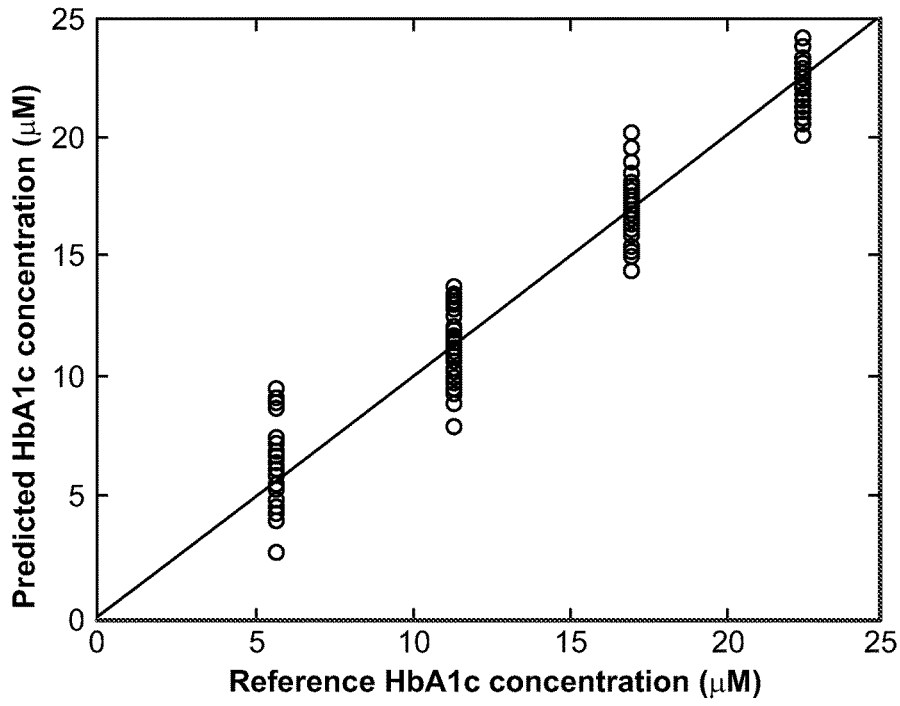

FIGS. 5A and 5B provide the results of leave-one-sample-out cross-validation analysis for the Hb and HbA1c constituents in the hemolysate models, respectively. This figure plots the predicted analyte concentration on the y-axis and the reference analyte concentration on the x-axis. The solid line indicates y=x and is provided to visualize the closeness of the measurements to an ideal linear response. As seen from the plot, the 16 hemolysate model samples had 11 distinct Hb and 4 distinct HbA1c concentration values with the range of glycated contributions in these samples covering and exceeding the normal physiological range of 3-11%. From FIGS. 5A-5B, the RMSECV values for Hb and HbA1c were computed to be 5.44 µM and 1.27 µM. Evidently these measurements show near-ideal linearity (between the predicted and reference concentration values) with the correlation coefficients of 0.99 and 0.98 for Hb and HbA1c, respectively.

The sample predictions have a fairly tight distribution (approximately centered around the reference concentration) indicating good reproducibility of the model predictions. In this context, the prediction precision (i.e. ratio of the standard deviation at a specific concentration to the reference concentration) was found to vary in the range of 0.07-0.30 for Hb (mean: 0.13) and 0.05-0.25 for HbA1c (mean: 0.12), respectively. This means that the prediction uncertainty (or "imprecision") was, on average, 12-13% of the actual concentration value. Expectedly, the prediction precision was better at higher concentration values for both analytes (due to the concomitant increase in SNR) and one would expect this number to be significantly lower at physiological levels.

In order to put the quantification capability of the models in perspective (and also to provide a common standard for comparison of the Hb and HbA1c models), the RPD values for the two datasets were computed. In general, for industrial applications of spectroscopy, a RPD value of 5 is typically considered to be good for quality control while a value larger than 6.5 may be used for process monitoring. Here, the RPD values for the Hb and HbA1c predictions were calculated to be ca. 6.3 and 4.8. This result indicates that the predictive power of the Hb model is superior to that of the HbA1c model, which is to be expected because of the higher spectral signal-to-noise ratio (SNR) resulting from the larger values of the Hb concentrations. Further, it can be inferred that both the Hb and HbA1c PLS models provide adequate predictive power, even for predictions at these extremely low concentration ranges.

Hemolysate model system measurements show that the method provides good prediction accuracy and precision for both analytes at concentrations which are less than typically encountered physiological levels by 2-3 orders of magnitude. The SNR or lowest analyte detection limits, are likely to be improved. For example, application of feature selection coupled with incorporation of advanced chemometric methods can boost the prediction accuracy of the calibration model.

The topography of the analyte deposits and their impact, if any, on the reproducibility of the measurements was analyzed. Based on the above precision computations, one would expect that there would be substantial overlap observed between the replicate measurements from a single drop-coated deposit. However, the critical question that remains unanswered at this juncture is what are the distributions of the two analytes across the ring width and, consequently, what is the ideal spot for DCDR measurements.

To characterize this in greater detail, 2D spatial Raman mapping on a representative hemolysate model deposit (where Hb concentration was 25.9 µM and the corresponding HbA1c concentration was 5.6 µM) was performed. Based on the details of the ring formation, the inner part of the coating ring was mapped to its central portion in order to avoid the lack of reproducibility usually associated with the outer perimeter of the ring (arising primarily from the desiccation of the proteins in this region). Using the previously developed calibration models, the spectral dataset was converted to a 2D matrix of concentration predictions for both Hb and HbA1c to allow the visualization of potential differences in distribution (organization) of the molecules in the edge region.

Figure 6A:
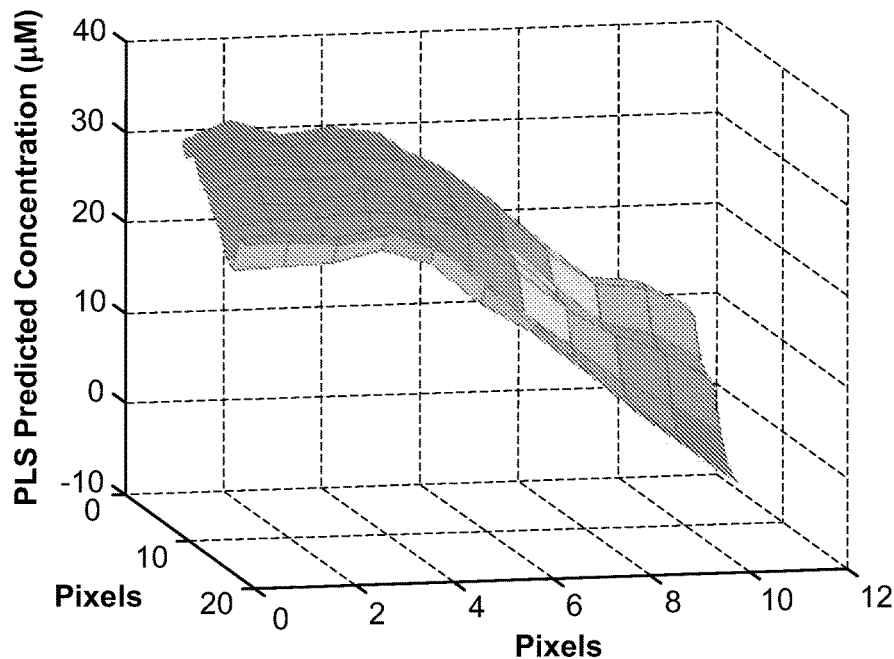
FIGS. 6A and 6B: 2D spatial Raman mapping based concentration prediction results for a representative hemolysate model for: (A) Hb and (B) HbA1c; the reference Hb and HbA1c concentrations are 25.9 µM and 5.6 µM, respectively, for this sample. The field of view is 44×44 µm with a pixel-to-pixel distance of 4 µm.
Figure 6B:
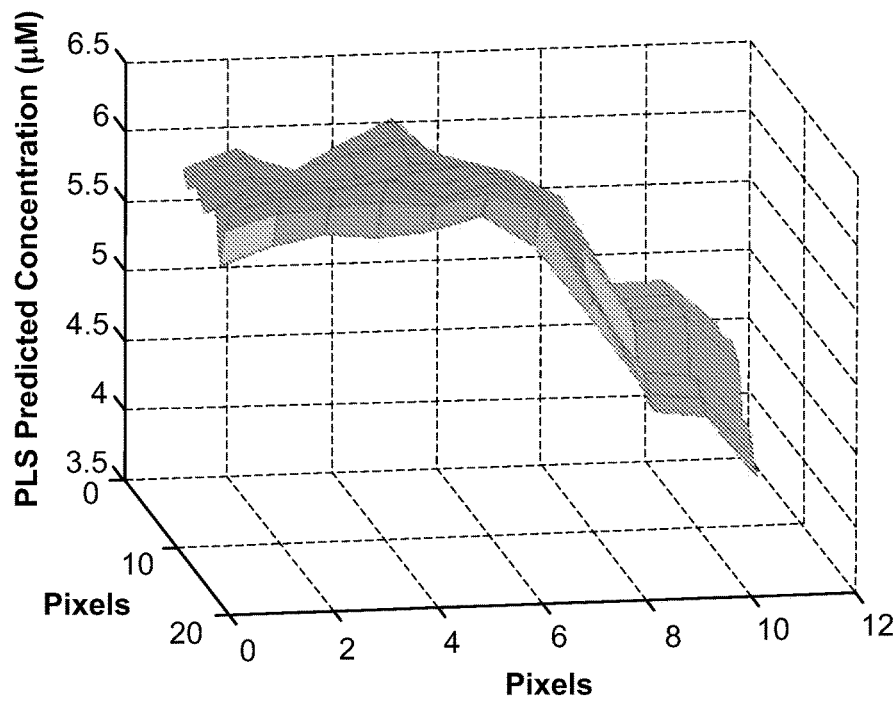

FIGS. 6A-6B shows the results of 2D mapping of a 44×44 µm field of view (pixel-to-pixel distance of 4 µm). From FIG. 6A, observe the high degree of consistency between point-to-point measurements, especially at a constant radial distance from the center of the deposit. Specifically, it was computed that the point-to-point deviation at any radial distance is less than 5% of the mean value (3×3 pixel average) for both analytes. Importantly, it was also found that the reference values of the analyte concentrations are reproduced with high fidelity at the center of the ring, i.e. the center of the ring displays a consistent value of ca. 25.5 µM and 5.5 µm for Hb and HbA1c, respectively.

More interestingly, the distribution profiles for both Hb and HbA1c are remarkably similar in the ring deposit. The similarity in profiles stems from their comparable molecular masses, which reduces any separation in the protein distribution that may otherwise have been caused by the flow in the drying droplet. This result is closely related to the previous precision results in the hemolysate models. It is evident that inhomogeneous distributions for the two analytes in the ring deposit would likely have adversely impacted the acquired Raman spectra, which in turn would have introduced significant uncertainty in the PLS predictions beyond the currently obtained levels. Nevertheless, in measurements of small analyte concentrations (where chances of inhomogeneity increase) it is advisable to average spectra acquired from multiple points in the ring center to increase signal-ltonoise ratio as well as to compensate for potential variations in protein distribution. Note that the field of view in FIGS. 6A and 6B form about half the total ring width of this deposit. Mapping results from the center-to-outside region of the ring displayed a similar, but not identical, profile as that of FIGS. 6A and 6B, albeit with slightly higher point-to-point variations.

The present invention uses an analytical method (non-enhanced Raman spectroscopy) for quantitative detection of HbA1c in single protein solutions as well as in hemolysate models. Given its linear response, high prediction accuracy and precision, the method can serve as a complementary tool to other more established analytical techniques, such as HPLC and immunoassay measurements, for detection of glycemic markers. Indeed, other methods of analysis are contemplated by the multimodal microscopy system, which is also provided by the present invention. PCT Application No. US2011/046750, herein incorporated by reference in its entirety, provides details regarding analytical methods used in conjunction with the present invention.

In the present system, drop coating deposition Raman-based selective detection and quantification of HbA1c, an important glycemic marker, at significantly lower concentration levels in comparison with typically observed physiological values. Investigations have also systematically considered the detection of HbA1c in hemolysate model systems. The spectra obtained from micro-liter aliquots of the samples were highly reproducible (as revealed from both point measurements and spectral mapping) and did not suffer from significant fluorescence background commonly associated with conventional Raman scattering.

To detect and quantify this important glycemic marker at remarkably low concentrations provides for measurement of glycosylation processes as well as establish analytical tools for clinical usage. The present methods provide for clinical use given the absence of significant sample preparation requirements coupled with the ability to perform precise and accurate measurements with small sample volumes. Preferred embodiments provide hemolysate samples and subsequently on whole blood samples. Processing steps prior to spectroscopic characterization, such as ultrafiltration or suitable microfluidic separation of analyte molecules depending on their respective diffusion coefficients (e.g. laminar fluid diffusion interface (LFDI) are contemplated as well.

Additionally, this method provides for quantifying of glycated albumin, which can be used by clinicians for an intermediate term marker for glycemic control (~14-17 days). Glycated albumin has a stronger correlation with the presence and severity of coronary artery disease (resulting from diabetic vascular complications) in comparison to HbA1c. Moreover, determination of both glycemic markers (namely HbA1c and glycated albumin), simultaneously, can provide useful data, because of the different 'lifetimes' of these molecules and because of the different interferences. If the two values are not concordant, it can necessitate further measurements before interpreting either value as reflecting the true long-term glucose profile. This system provides for clinical feasibility of performing non-enhanced Raman measurements for the detection of alternate glycemic markers and, in parallel, to reduce the current measurement system to a miniaturized form that is viable for routine use in clinics, laboratories and in patients' homes.

Another preferred embodiment of the present invention relates to spectral measurements of albumin and glycated albumin. These measurements can be performed using a method of concentrating the same using a ring pattern, where the analytes (e.g. proteins) are deposited from the drying drop. Herein, systematic experimental studies were initiated to achieve a two-fold objective. First, the method is assessed in conjunction with multivariate chemometric methods, to clearly distinguish pure albumin and glycated albumin samples. Second, the quantitative ability of this method to precisely and accurately predict the concentration of glycated albumin at physiologically relevant levels and below is described. Single Raman spectroscopic measurements were performed on multiple drop-coated samples derived from a wide range of albumin and glycated albumin solutions, respectively. The acquired spectra were first examined for specific Raman bands and, subsequently, to discriminate between the samples. Subsequently, a regression methodology was employed to quantitatively predict glycated albumin concentrations from the Raman spectroscopic measurements obtained from drop-coated depositions and to establish the prediction accuracy, precision and limit of detection of the method. In addition to the spectroscopic measurements, 2D spatial Raman mapping was performed on representative drop-coated samples to investigate the uniformity of the distribution of the analytes of interest, such as albumin and glycated albumin.

A Raman spectroscopic system equipped with a 785 nm CW Ti:Sapphire laser (3900S, Spectra-Physics), which was pumped using a frequency-doubled Nd:YAG laser (Millennia 5sJ, Spectra-Physics), as described previously can be used. A liquid-nitrogen cooled CCD (LN/CCD 1340/400-EB, Roper Scientific) combined with a spectrograph (Kaiser Holospec f/1.8i) was used for collection of the spectra. The water immersion objective lens (Olympus UPLSAPO60XWIR 60×/1.20) used for these measurements focuses the laser to a spot size of approximately 1 µm on the geometric center of the drop-coated ring and collects the backscattered Raman light. Due to the non-absorptive nature of the albumin and glycated albumin deposits, the power at the sample can be kept relatively high at ca. 30 mW without the possibility of optical and/or thermal damage to the samples. The detailed description of this system can be found in Kang, et al., BIOMEDICAL OPTICS EXPREss, 2(9): 2484-2492 (2011) incorporated herein by reference in its entirety; however it should be noted that a simpler Raman measurement system can be used as described herein.

Figure 7C:
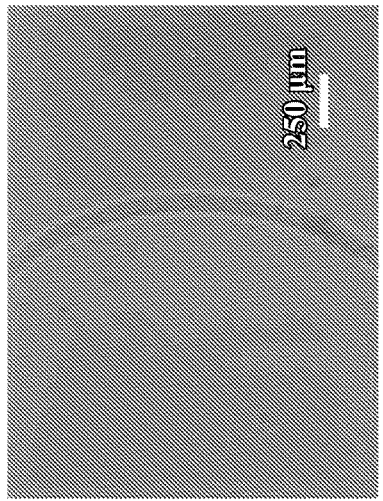
FIGS. 7A-7F are bright field images of the drop-coated deposition rings obtained from air-drying of aqueous glycated albumin samples; the analytes are concentrated in the annular ring; the samples (7A-7F) are arranged in the order of descending concentration levels of glycated albumin, which is reflected in the widths of the corresponding rings.
Figure 7F:
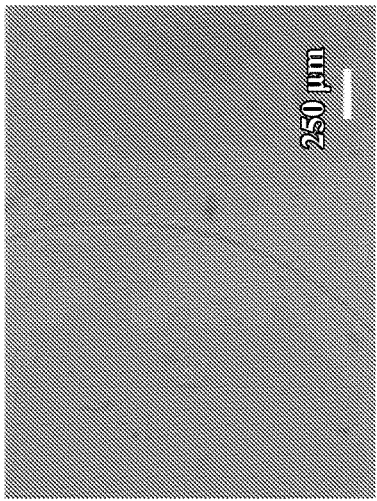
Figure 7B:
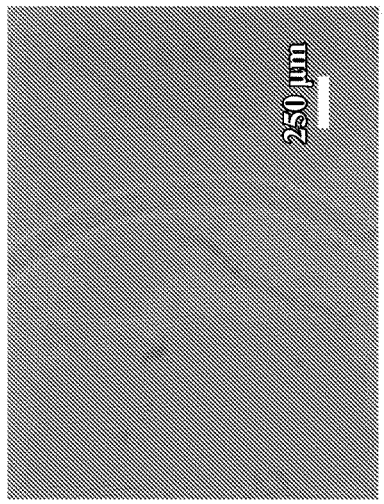
Figure 7E:
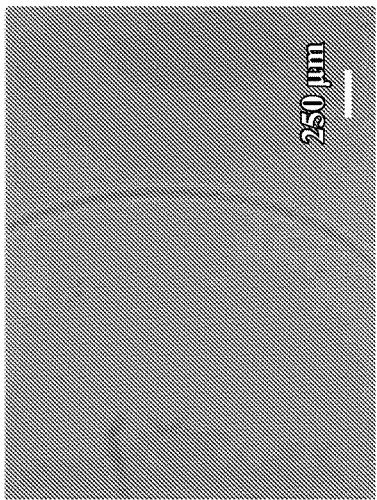
Figure 7A:
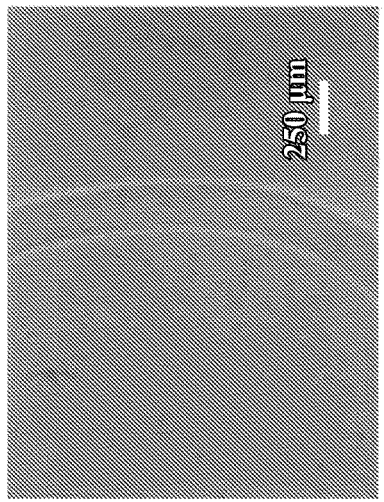
Figure 7D:
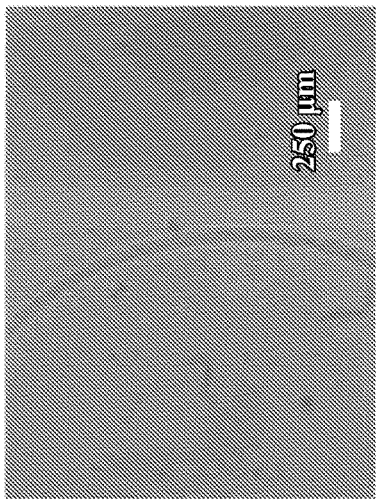

Lyophilized powder samples of human serum albumin and glycated albumin were obtained from Sigma-Aldrich (St. Louis, Mo., USA). The aqueous solutions of albumin were prepared in the range of 23-750 µM (the typical physiological range is between 3.5-5.5 g/dL or, ca. 510-710 µM). Correspondingly, glycated albumin samples were formulated with concentrations in the range of 7-250 µM (typical physiological values are 15-30% of the above mentioned albumin concentrations). All sample preparations are performed using high purity PESTANAL water (Fluka) to ensure the reproducibility of the measurements. Drop-coated depositions were prepared by pipetting aliquots (4 µL) of the prepared solutions on quartz coverslips (which were used to avoid the strong fluorescence interference of glass) and air-drying for approximately 20 minutes. The air-dried rings had widths in the range of 40-700 µm and scaled roughly in a linear fashion with respect to the concentrations (consequently, the albumin samples had larger ring widths in comparison to the glycated albumins samples). FIGS. 7A-7F show (portions of the) annular rings obtained from the glycated albumin samples after solvent evaporation, where FIG. 7A shows a sample with the highest analyte concentration and FIG. 7F shows a sample with the lowest.

The acquisition time of the Raman spectra was about 10 seconds or less. For the classification and regression analysis, spectra were collected from each sample at three different points in the direction of the are of the ring, with five replicate measurements at each location. The spectroscopic measurements were performed on the approximate center of the annular ring where the analytes accumulate due to solvent evaporation. Note that this is different from the center of the ring, where little or no analyte deposition takes place (as confirmed by the lack of analyte-specific Raman spectral features in this region). Further mention of the drop-coated deposit refers to the analyte-rich annular region, unless otherwise noted. In addition for the investigation of the uniformity, a total of 100 spectra were collected over a 80×80 µm field of view with 8 µm inter-point distance (2D spatial Raman mapping). The spectra acquired from these measurements were subject to vertical binning and cosmic ray removal. No background correction was taken into consideration for the ensuing quantitative analysis due to the possibility of incorporation of spurious artifacts.

To analyze the classification ability of the proposed method between albumin and glycated albumin samples, principal component analysis (PCA) (part of the Statistics Toolbox in MATLAB R2010b (MathWorks, Natick, Mass.)) was performed on the entire dataset containing 180 spectra in all. In particular, 90 spectra were acquired from 6 different samples of albumin and glycated albumin, each of which had a different concentration in the ranges mentioned above. Principal component analysis (PCA) is a dimension reduction technique, which uses an orthogonal transformation to convert a set of observations of closely correlated variables into a set of values of uncorrelated variables called principal components (PC). The first few principal components (each PC is orthogonal to the preceding one) account for a high degree of the net variance and is often used for visualizing the primary differences between the classes. Logistic regression on the relevant principal components was pursued to obtain a separation plane between the samples and to ascertain the degree of classification accuracy. Logistic regression is employed here to correlate the principal component scores with the sample classes (namely, albumin and glycated albumin).

Moreover, in order to illustrate the capability of DCDR to provide quantitative measurements of these analytes, partial least squares (PLS) regression was employed. A leave-one-sample-out cross-validation procedure was used to assess the reproducibility of the measurements as well as to evaluate the predictive power of the glycated albumin data. In the leave-one-sample-out cross-validation routine, one sample is left out when developing the calibration model and the resultant model is used to predict concentrations of the left out sample spectra. This procedure is repeated until all samples are left out and all concentrations are predicted.

Specifically to gauge the reproducibility of the measurements, a leave-one-sample-out PLS model (developed on the 75 spectra from 5 corresponding samples) was used to predict the concentrations for the 100 spectra collected over a 2D area of the ring on a representative glycated albumin sample.

Similarly, for the quantification measurements of glycated albumin, the calibration models are developed using 75 spectra (5 samples with 15 spectra per sample) and the predictions are performed on the remaining 15 spectra (1 sample) to obtain 15 predicted concentrations. This method is repeated until all the glycated albumin samples (and spectra therein) are accounted for. Here, three figures of merit, namely relative error of prediction (REP), relative standard deviation (RSD) and limit of detection (LOD), were computed. The REP and RSD numbers correlate directly with the accuracy and precision of DCDR predictions, respectively. In the following, we provide the equations used for computing the figures of merit:

(i) Average Relative Error of Prediction, REP:

$$REP(\%) = \frac{100}{N} \sum_{i=1}^{N} \left| \frac{\hat{c}_i - c_i}{c_i} \right| \quad (1)$$

where N is the number of spectra in the dataset, $c_i$ is the reference concentration and $\hat{c}_i$ is the predicted concentration.

(ii) Average Relative Standard Deviation of Predicted Concentrations, RSD:

$$RSD(\%) = \frac{100}{N_{conc}} \sum_{k=1}^{N_{conc}} \frac{\sigma_{c_k}}{c_k} \text{ where } \sigma_{c_k}^2 = \sum_{i=1}^{p} \frac{(\hat{c}_{ik} - c_k)^2}{p-1} \quad (2)$$

where $N_{conc}$ is the number of distinct concentrations in the dataset, p is the number of spectra per concentration and $\sigma_{ck}$ is the standard deviation obtained at concentration $c_k$.

(iii) Limit of Detection, as Per the IUPAC Definition, is Computed from the Best Fit Line Obtained Between Predicted Concentrations and Reference Concentrations:

$$LOD(\mu M) = 3 \frac{s_{y/x}}{slope} \text{ where } s_{y/x} = \left[ \frac{\sum_i (\hat{c}_i - c_i)^2}{N-2} \right]^{1/2} \quad (3)$$

where $s_{y/x}$ is the standard deviation of the residuals and is a measure of the average deviation of the predicted values from the regression line.

Figure 8:
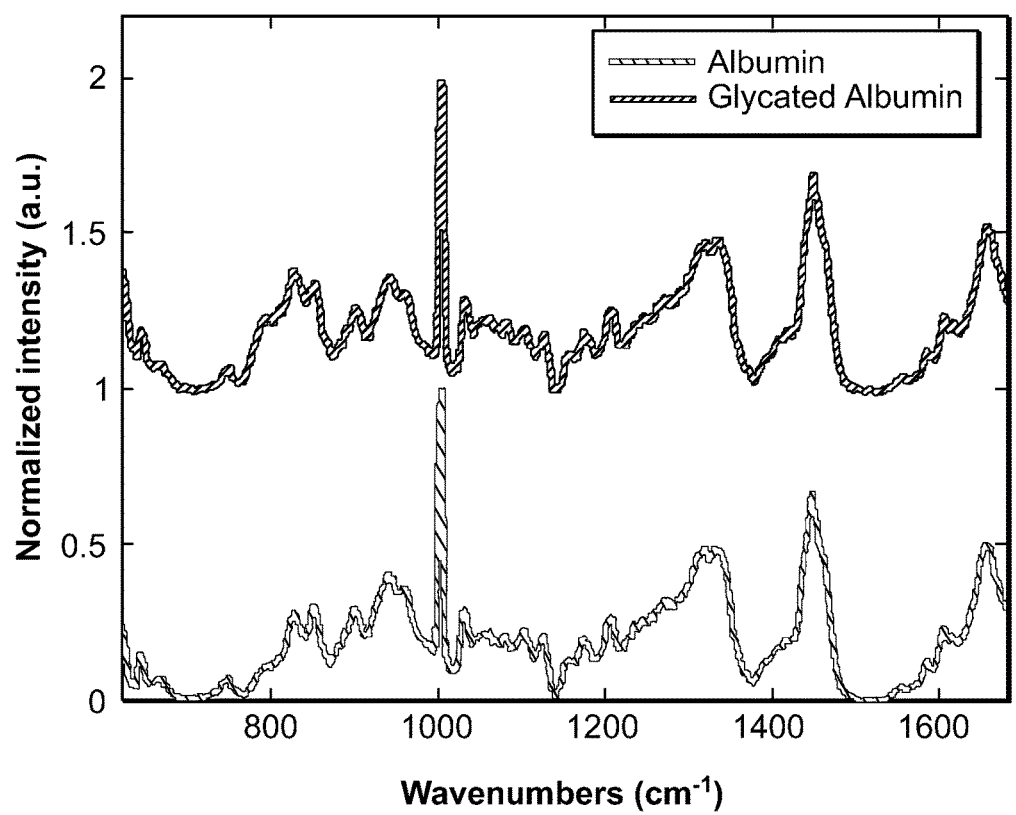
FIG. 8: Raman spectra acquired from the drop-coated albumin and glycated albumin samples derived from 750 µM and 250 µM concentration solutions, respectively (the spectra are normalized and offset for the sake of clarity).

FIG. 8 shows Raman spectra acquired from typical drop-coated depositions of human serum albumin (green) and glycated albumin (red) solutions. For the sake of visual representation, the plots shown in FIG. 8 were subject to 5 spectra averaging from each sample and baseline-removal. Note that the baseline-removed spectra were not used for any of the following analysis.) The features observed in our (DCDR) albumin spectrum are consistent with those previously reported for albumin solutions. A summary of the wavenumbers and their corresponding tentative Raman band assignments is given in Table 1.

TABLE 1

Chemical assignments of vibrational modes for the Raman spectra acquired from drop-coated deposition of human serum albumin sample

| Wavenumber (cm$^{-1}$) | Tentative Band Assignments |
| --- | --- |
| 1655 | Amide-I |
| 1616 | Tyr |
| 1605 | Phe |
| 1584 | Phe |
| 1447 | $\delta(CH_2)$ |
| 1335 | $\delta(CH)$ |
| 1319 | $\delta(CH)$ |
| 1208 | Tyr + Phe |
| 1172 | Tyr |
| 1157 | $\upsilon(CN)$ |
| 1125 | $\upsilon(CN)$ |
| 1102 | $\upsilon(CN)$ |
| 1089 | $\upsilon(CN)$ |
| 1031 | Phe |
| 1002 | Phe |
| 960 | $\upsilon(CC)$ |
| 940 | $\upsilon(CCN)_{sym}$, $\upsilon(CC)$ |
| 899 | $\upsilon(CC)$ |
| 850 | Tyr |
| 828 | Tyr |
| 667 | $\upsilon(CS)$ |
| 643 | Tyr |

In particular, note the presence of the following key features: 1655 cm$^{-1}$ Amide-I band, 1447 cm$^{-1}$ CH$_2$ deformation band, 1002 cm$^{-1}$ phenylalanine band and the tyrosine doublet at 828 and 850 cm$^{-1}$. The Amide-I band is a characteristic feature of the α-helical (secondary) conformation of the polypeptide backbone stemming mainly from peptide C=O stretching vibration. This is important because any change of this band indicates a modification in the secondary structure of human serum albumin, which is predominantly an alpha-helical molecule (67%). Furthermore, the strong phenylalanine peak at 1002 cm$^{-1}$ is reflective of the presence of 31 phenylalanine residues present in albumin (tryptophan may provide a small contribution to the intensity of the 1002 cm$^{-1}$ band as well).

Expectedly, the glycated albumin spectrum does not exhibit any gross differences in comparison to the albumin spectrum. Note that (non-enzymatic) glycation of albumin occurs at multiple sites corresponding to the arginine, lysine and cysteine residues, which can be attributed to their high nucleophile properties. Since the Raman signature of albumin does not have significant contributions from these residues, one would anticipate that the corresponding glycation-induced changes would be subtle. Nevertheless, note that these changes, although relatively small, are consistent and, as such, provide sufficient information to distinguish between albumin and glycated albumin samples. Specifically, such small changes are routinely detected using multivariate chemometric algorithms, which can be employed in the following analysis. It is also worth mentioning that glycation measurements have indicated the conversion of albumin into a high β-sheet structure—another potential marker that can aid the classification of glycated and unglycated samples.

Figure 9A:
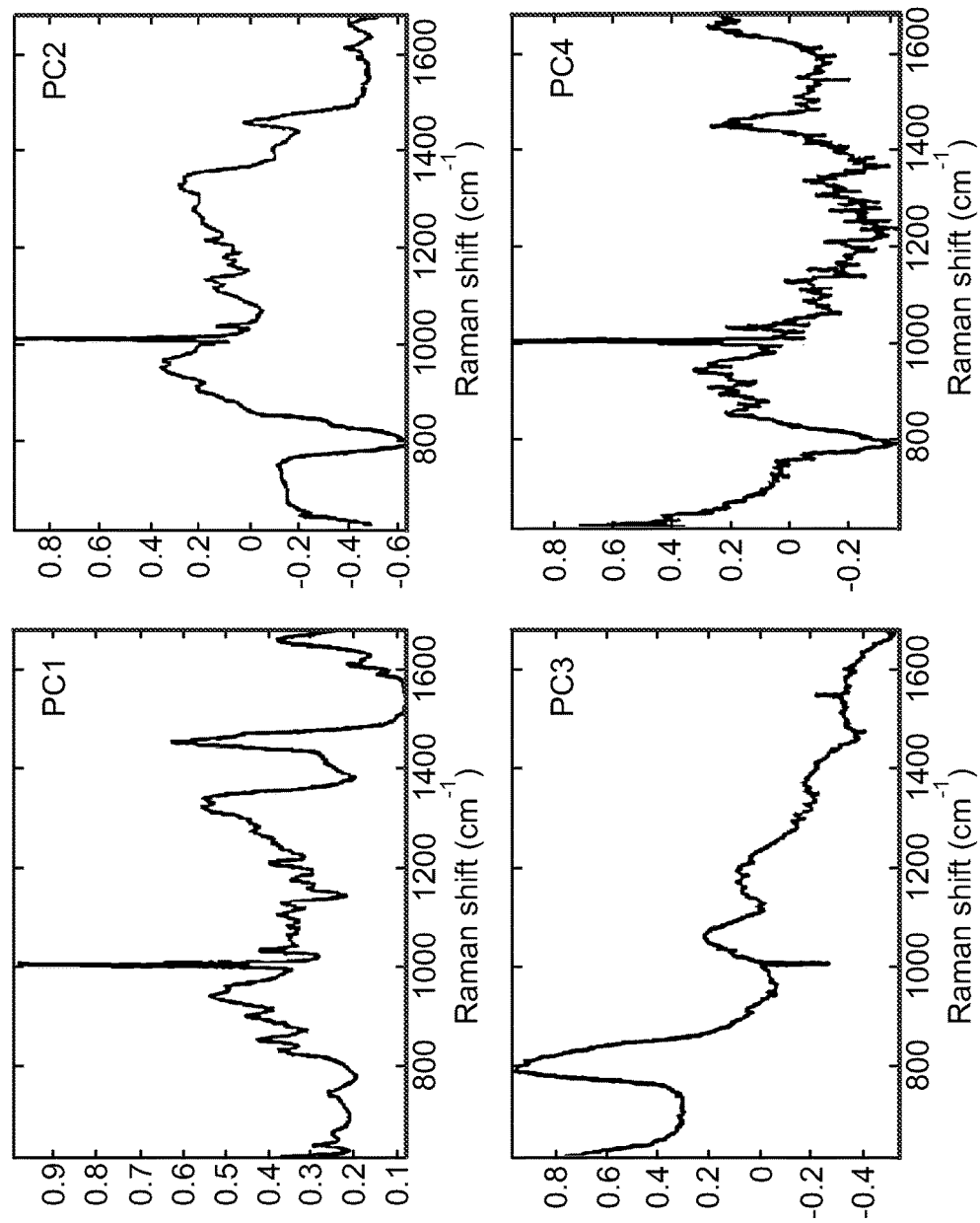
FIG. 9A: The first four principal components corresponding to the entire spectral dataset acquired from the albumin and glycated albumin drop-coated deposition samples. These four principal components, combined, explain 99.74% of the net variance in the dataset.

To this end, PCA was employed to visualize the underlying information from the multivariate spectral dataset, comprising both albumin and glycated albumin samples (90 spectra from 6 samples at different concentrations for each of the analytes). FIG. 9A gives the first four principal components (which together account for 99.74% of the net variance). PC bears a striking resemblance to the pure albumin spectrum (and by extension to the glycated albumin spectrum, albeit to a somewhat lesser extent—especially in the 780-850 cm$^{-1}$ region of the tyrosine doublet). PC2 retains some of the key features seen in PC1, although in different proportions. A feature is observed at ca. 792 cm$^{-1}$, which stems from the differences in the aforementioned shoulder region in the tyrosine doublet between the glycated and unglycated samples. This feature is also present in a prominent manner in PC 3 and 4. In addition, these PCs have an interesting feature at ca. 1542 cm$^{-1}$, which was not noted in the list of prominent bands in Table 1.

Figure 9B:
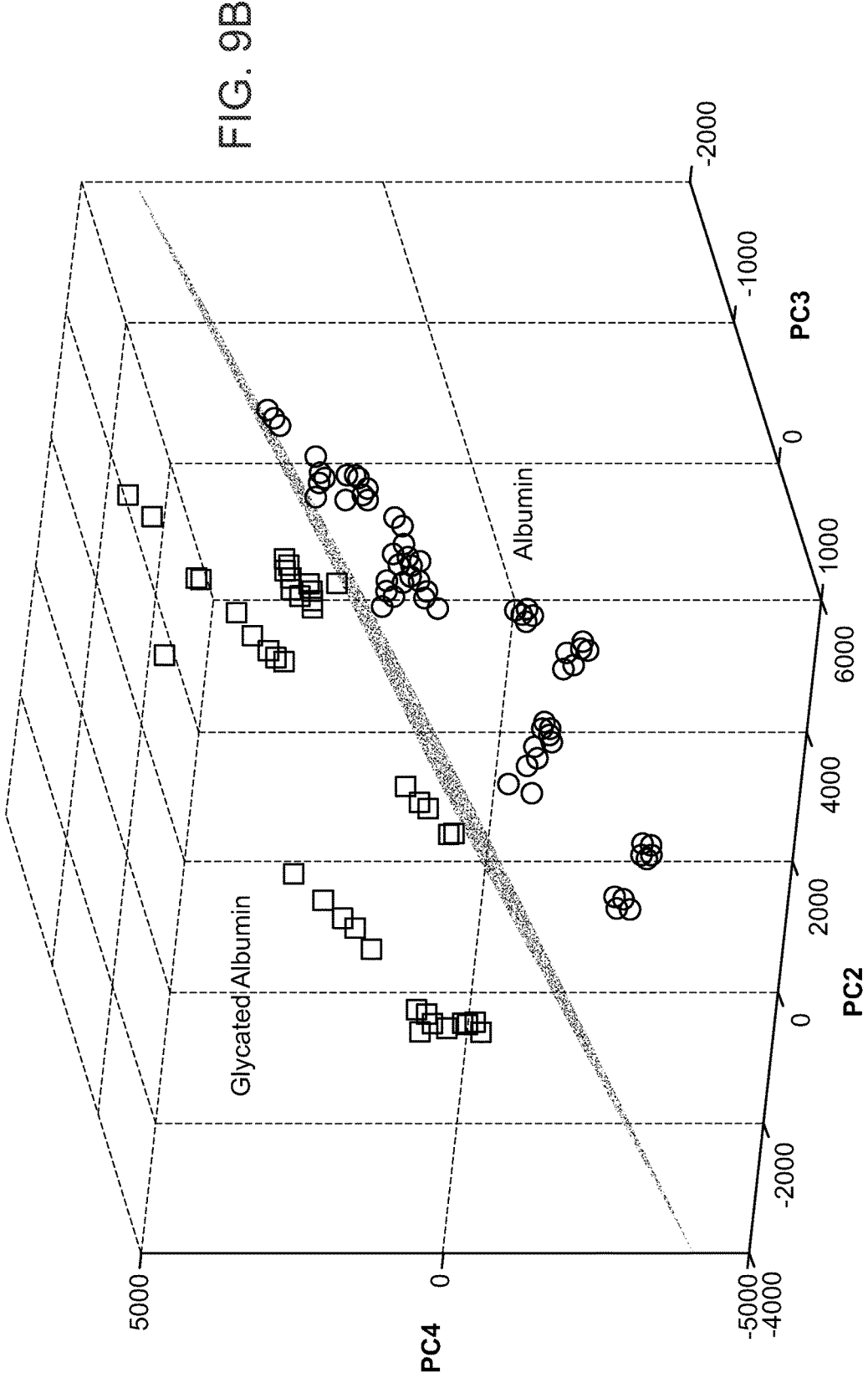
FIG. 9B: Scores plot corresponding to principal components 2, 3 and 4 for the spectral dataset acquired from albumin and glycated albumin drop-coated rings; the albumin and glycated albumin samples are indicated by circles and squares, respectively; the optimal plane of separation, as shown here, is constructed using a logistic regression algorithm.

The corresponding scores plot for PCs 2, 3 and 4 is given in FIG. 9B. PC was excluded from this 3D plot because of its relatively lower discriminative power between the two sets of samples in comparison to the PCs employed here. Remarkably, a clear separation is shown between the albumin and glycated albumin samples. To measure the discrimination ability of this method, logistic regression on the scores of PC 2, 3 and 4 (i.e. score$_2$, score$_3$ and score$_4$, respectively) was used. The optimal separation plane, based on these three parameters, was computed to be:

$$3.9225 - 0.0027\text{score}_2 + 0.0023\text{score}_3 + 0.0041\text{score}_4 = 0 \qquad (4)$$

This logistic regression algorithm gave a classification accuracy of 100%, as can be seen from FIG. 9B. To test whether such a classification result can be obtained from spurious correlations (such as system drift during measurements), two control measurements were performed. First, the "albumin" and "glycated albumin" labels were assigned randomly to the 180 spectra, without any regard for their actual origin. The new "optimal" logistic regression algorithm barely gave 55% classification accuracy (which in this binary classification problem is akin to a random guess). This underlined the inability of the algorithm to predict the randomly assigned classes. Subsequently, class labels were assigned in correlation with the measurement order of the samples to investigate the possibility of temporal correlations (e.g. that stemming from system drift). In other words, we assigned the first 90 samples as albumin and the last 90 as glycated albumin (whereas the spectral measurements were performed in an arbitrary manner between the albumin and glycated albumin samples). Here, too, the "optimal" logistic regression algorithm displayed poor performance, and the overall classification accuracy was computed to be ca. 60%. Taken together, the actual logistic regression performance and the control measurements indicate that the chemometric methods can reliably predict class labels based on differences in spectral features between albumin and glycated albumin samples. The measurements indicate the robustness of DCDR in combination with multivariate classification to chance correlations.

Figure 10:
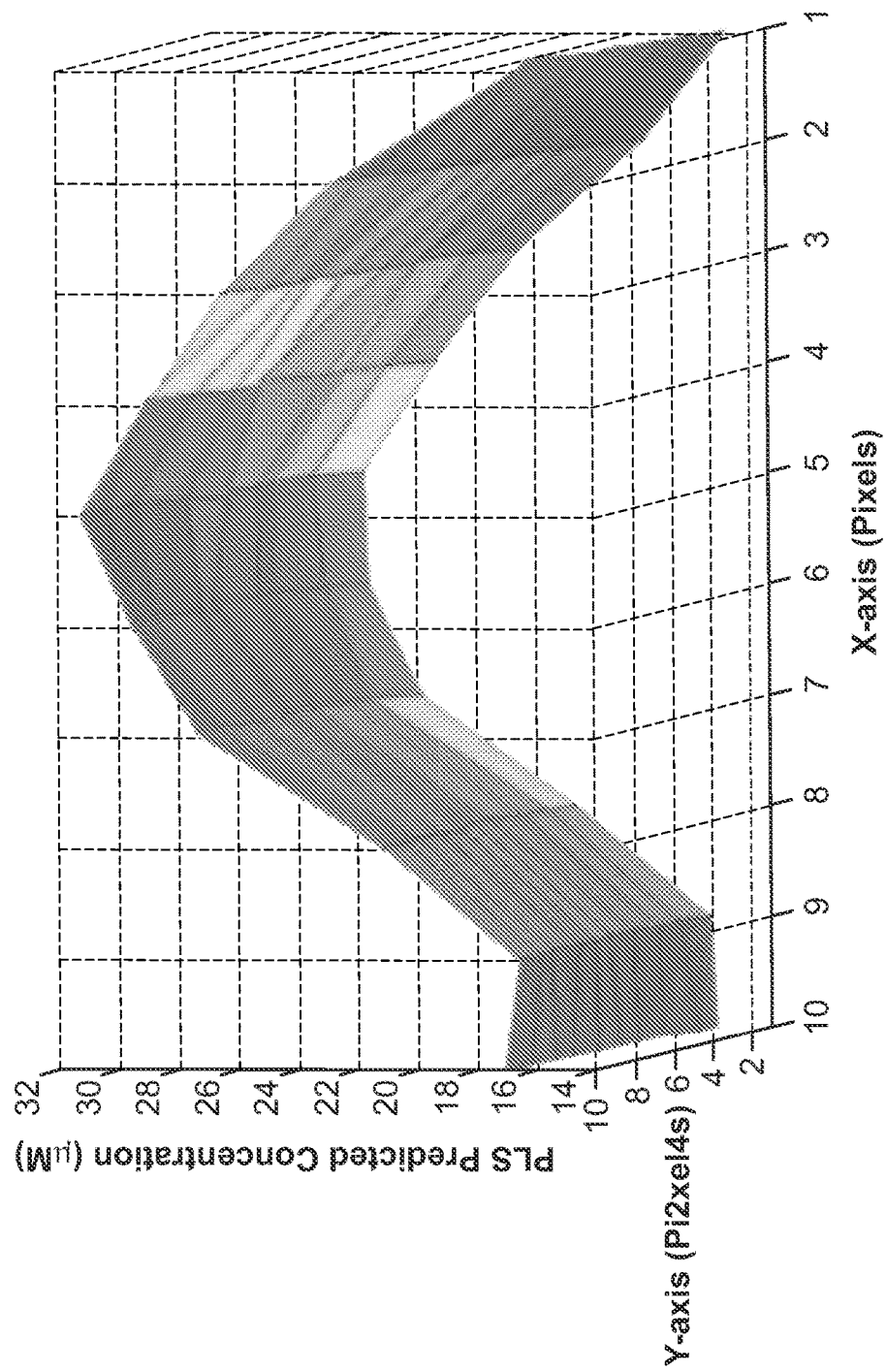
FIG. 10: 2D spatial Raman mapping based concentration prediction results for a representative glycated albumin drop-coated ring. The reference glycated albumin concentration in this sample is 31.25 µM. The field of view is 80×80 µm with a pixel-to-pixel distance of 8 µm. Pixel 1 on the X-axis is located closer to the center of the ring (inner periphery) and pixel 10 is farthest away from the ring center.

Since PCA and logistic regression showed excellent discrimination ability from the DCDR spectra, a multivariate regression approach (PLS) was used to analyze the predictive power of the glycated albumin data. Before this, it is important to characterize the reproducibility of the measurements by computing the potential variations in the radial and, more importantly, in the angular direction. Here, 2D spatial Raman mapping-based predictions were performed on a representative glycated albumin sample (reference analyte concentration=31.25 µM) using PLS calibration models developed on the other 5 sample spectra. FIG. 10 plots the results of this analysis for the 100 spectra acquired over a 80×80 µm area of the annular ring. The profile along the radial direction (X-axis) shows an approximately symmetric shape with a steeper descending outer part in comparison to the more gradual descent in the inner part of the ring. This is consistent with previous observation of complete desiccation at the outer perimeter of the ring, primarily from oscillation of the droplet contact line. On the other hand, there is a high degree of consistency between the predictions along the Y-axis, which for small distances (such as those considered here) provides a reasonable approximation for the angular direction. The coefficient of variation (i.e. the ratio of standard deviation to the mean of the predicted concentrations) along the Y-axis is calculated to be in the range of 0.014-0.074 with a mean of 0.038. This demonstrates the reproducibility of the spectral predictions along the analyte-rich annular region of the ring, when the measurements are performed at a constant radial distance. Importantly, it was also observed that the reference values of the glycated albumin concentrations are reproduced fairly accurately near the center portion of the ring, i.e. the average of the predicted concentration over pixels 5 and 6 on the X-axis is 29.9 µM. Clearly, the absence of significant inhomogeneity in the drop-coated samples substantially increases the reliability of the systematic assessment of the prediction accuracy and precision across a wide range of concentrations.

Figure 11:
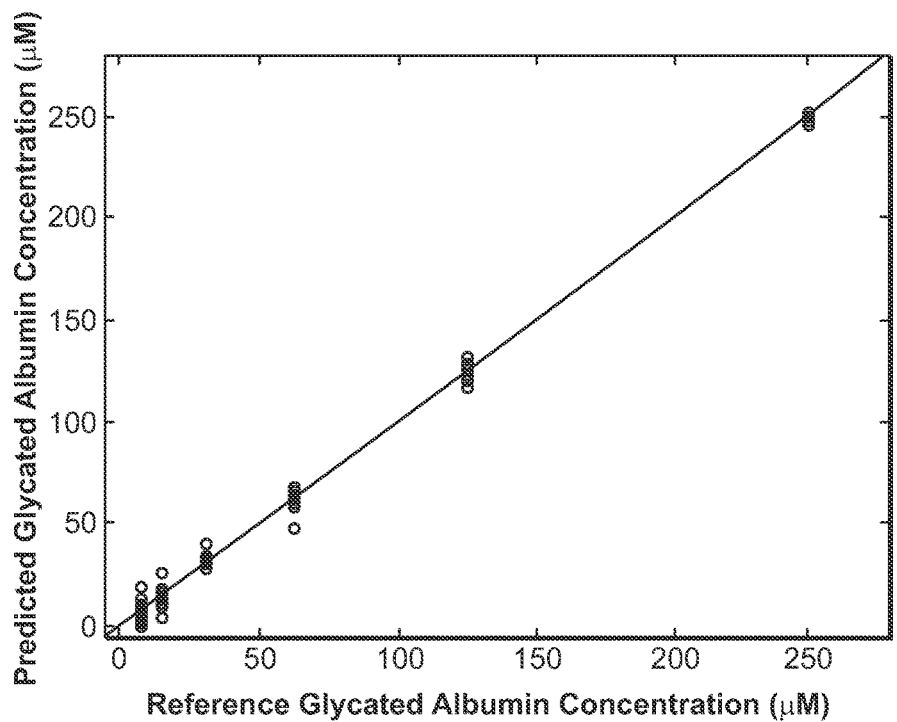
FIG. 11: PLS prediction results of glycated albumin samples. Prediction results obtained using partial least squares (PLS) regression on glycated albumin samples. The solid line denotes y=x values.

FIG. 11 shows the results of leave-one-sample-out cross-validation for the glycated albumin samples, where the reference and PLS predicted concentrations are given along the X- and Y-axis, respectively. The solid black line illustrates y=x and is given to explicitly understand the linearity of the response (or the lack thereof). From FIG. 11, it is evident that the predicted values show excellent agreement with the reference concentrations and the corresponding correlation coefficient between these two set of values is calculated to be 0.9986. Further, the REP was calculated to be ca. 16%, showing thereby that PLS provides very accurate predictions for the DCDR glycated albumin data over the entire concentration range of 7-250 µM. When the glycated albumin sample having 7 µM concentration is omitted from the dataset (as it is below the limit of detection of our system as discussed below), the REP value drops to 8.5% (and an incremental rise in the correlation coefficient to 0.9987).

Figure 12:
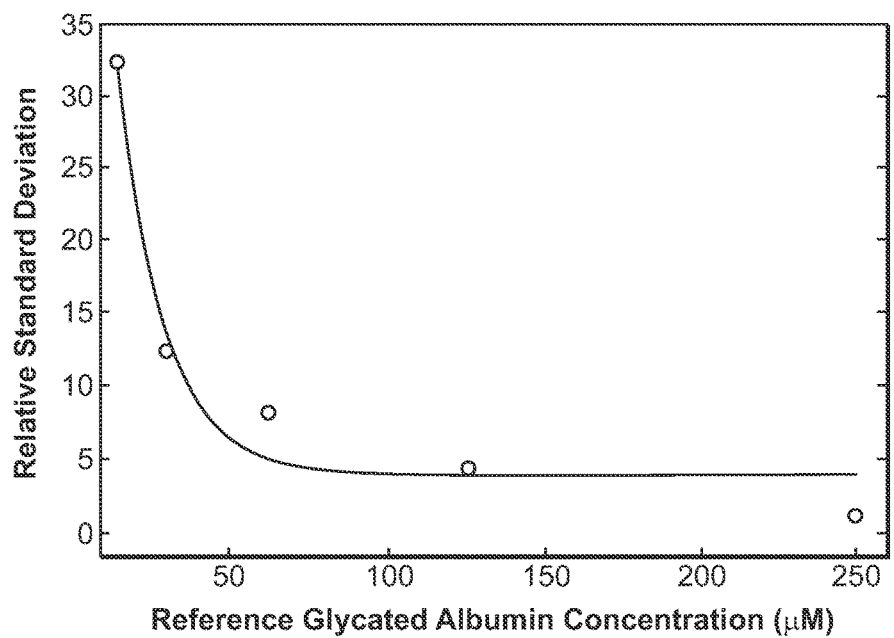
FIG. 12: Relative standard deviation plot of precision for glycated albumin determination. Plot of precision as a function of reference glycated albumin concentration. The circle gives the values computed from the experimental measurements and the solid curve represents the best-fit exponential curve.

Finally, the precision of the measurements was evaluated using the RSD metric. For the entire concentration range, the precision was observed to be 21.56%. Notably, when the 7 µM glycated albumin sample was not included in this analysis, the RSD metric reached a clinically acceptable value of 11.6%. Naturally, the precision gets worse as the concentration of the analyte decreases—a common characteristic of any spectrochemistry measurement. This aspect is revealed in FIG. 12, where the RSD is graphically plotted as a function of the reference glycated albumin concentration.

The LOD was determined using the standard deviation of the residuals and the slope of the regression line, the so-called calibration plot method. Here, the LOD for glycated albumin was computed to be 13.7 µM, which is evidently higher than the lowest concentration used for these measurements (7 µM) but lower than the remaining sample concentrations. More importantly, this value is nearly 4 times less than the lowest physiological concentrations likely to be encountered in clinical settings (ca. 50 µM). Quantitatively speaking, the RSD is also 33% at the limit of detection (as per the IUPAC definition or 3σ detection limits) and therefore one can graphically extrapolate the RSD versus concentration plot to arrive at the LOD. Here, using this alternate method, the LOD value was found to be 14.7 µM. The small deviation from the previous value (13.7 µM) can be attributed to the deviation from an ideal exponential fit seen in FIG. 12. Nevertheless, both methods generate very close numbers indicating the system's capability of measuring very low concentrations of glycated albumin.

Thus, preferred embodiments provide analytical procedures for reproducible identification and accurate quantification of glycated albumin. The reagent-free and real-time nature of this method, combined with its high degree of prediction accuracy and precision and low limit of detection, enable the application to clinical settings. Glycated albumin measurements in serum and in whole blood samples can be performed. The measurements in serum samples are aided by the fact that albumin is the most abundant protein in the serum and therefore the interference from other analytes, especially for Raman measurements, are greatly reduced. Furthermore, with the similar molecular weights of albumin and glycated albumin in mixture samples, the DCDR ring structure formed from the solvent evaporation process is fairly homogeneous across the angular dimension. Additionally, in combination with the Raman-based characterization of protein glycosylation can be used with Raman and other spectroscopic modalities (such as 2D-IR absorption spectroscopy) for understanding the detailed structure and dynamics of albumin transformation caused by the presence of different analytes of interest, such as glucose and heavy metal ions.

To measure the levels of HbA1c in hemolysates and whole blood lysates from normal human subjects and diabetic patients, the following procedure can be used: Whole blood samples (drawn by standard venipuncture into an EDTA test tube) are subject to centrifugation to separate out the cellular components from the plasma and subsequently lysed, using a suitable lysing reagent or by changing the tonicity of the cell suspension, before performing DCDR. Once validated in the hemolysate samples, HbA1c determination in blood lysates can be performed by applying the lysing reagent directly to the whole blood sample, thereby eliminating the centrifugation step, although spectral interference may be higher due to the presence of serum analytes. To address any potential spectral interference from other analytes, appropriate feature selection mechanisms in combination with advanced classification tools can be used.

To measure glycated albumin, sample preparation is minimal. The sample can be drawn by standard venipuncture into a plain tube or a serum separator tube (a tube that contains a clot activating compound and, upon centrifugation, separates the serum from the cellular components of the blood). The protocol for obtaining serum from a blood sample involves the steps of allowing the sample to clot for 20 minutes, after which centrifugation occurs (e.g. 1000-1200×G for ten minutes; CLSI Standard H18-A3). If the sample is not in a serum-separator tube, it can be transferred to a separate tube to prevent contact with the cellular components.

Thus, the present invention uses optical spectral measurement to detect and quantify the concentration of glycated albumin, an important glycemic marker for long-term diabetes monitoring. Specifically, it can be demonstrated that application of drop-coating deposition Raman spectroscopy can accurately discriminate glycated albumin from the unglycated variant, even at low μM concentrations. Further, in conjunction with standard multivariate analysis methods, the limit of detection of the proposed approach for glycated albumin is nearly 4 times lower than the minimum physiological concentrations encountered in practice. In contrast to most of the existing detection methods for glycated albumin, this method is also timesaving, easy to perform, completely reagent free and requires little sample preparation. Predictive diagnostic value in multi-component mixtures is used, specifically, in serum and whole blood samples.

The combined determination of HbA1c and glycated albumin provides a uniquely powerful metric in estimating the "true" glycemic history of a patient—a feature that is currently lacking in most clinical laboratories globally. The differences in the lifetime of these two important glycemic markers provide details on the long-term glucose profile of a diabetic. Furthermore, the measurement of two markers can be imperative in certain clinical cases where one or the other may provide inaccurate estimates. For example, HbA1c values have been reported to underestimate the blood glucose levels in patients with hemolytic anemia, or those submitted to hemodialysis, whereas glycated albumin may not be an appropriate indicator for glucose excursion in pathologies that impact albumin metabolism, e.g. thyroid dysfunction and nephrotic syndrome. As a consequence, there is a significant clinical need for rapid and reliable glycemic history assessment that is (more) robust to other pathological changes. This clinical need can be addressed by utilization of this spectroscopic system.

The confocal Raman signal is delivered to an imaging spectrograph (HoloSpec f/1.8i, Kaiser Optical Systems and spectra are captured by a liquid nitrogen cooled CCD (LN/CCD-1340/400-EB, Roper Scientific). The confocal reflectance signal is delivered to a photomultiplier tube (PMT, H9656-20, Hamamatsu) and amplified by a PMT controller (CT169, Hamamatsu). Labview 8.2 software (National Instruments) and a data acquisition board (PCI-6251, National Instruments) are used to control the devices.

A form of quantitative phase microscopy (QPM) instrumentation, is Hilbert phase microscopy, that can be included in the system. A Mach-Zehnder interferometer is integrated into the scanning microscope. The laser beam is divided into object and reference beams and superimposed in front of the camera, which is also used for bright field imaging. Pixel to pixel distance of the camera is 2.2 μm, for example.

The off-axis interferogram from the Mach-Zehnder interferometer is processed using the standard Hilbert transform. Briefly, the interferogram is Fourier transformed and the first order signal is selected in Fourier space. The phase from the inverse transformed field gives the optical phase delays in the sample plane. To extract phase delay for the sample only, we separately measure the reference phase information without a sample in the field of view and subtract it from the phase delays for the sample. The phase resolution measured from the empty area without sample was 0.067 radians (~λ/100). The RBC has a relatively uniform sub-cellular structure. Assuming that the RBC is predominantly composed of hemoglobin, optical phase delays can be directly converted into RBC thickness.

Dominant spectra are calculated by principal component analysis and Raman images are reconstructed from their spatial distribution. For healthy RBCs, the hemoglobin Raman signal mainly dominates the spectra. Unlike healthy RBCs, malaria-infected RBCs contain additional major components such as malaria pigment (the hemozoin crystal), which can be used to indicate the progression of the disease. Composed of polymerized heme molecules, hemozoin has distinct iron-carboxylate bonds yielding a Raman signature different from that of hemoglobin. From the Raman images, hemoglobin and hemozoin regions can be clearly distinguished.

Figure 13A:
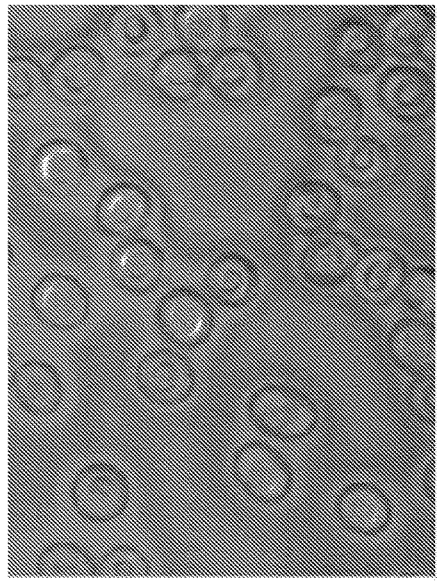
FIGS. 13A-13D: Illustrate a multimodal imaging including bright field imaging, confocal reflectance, and quantitative phase imaging as well as hemoglobin distribution from Raman mapping, respectively.
Figure 13B:
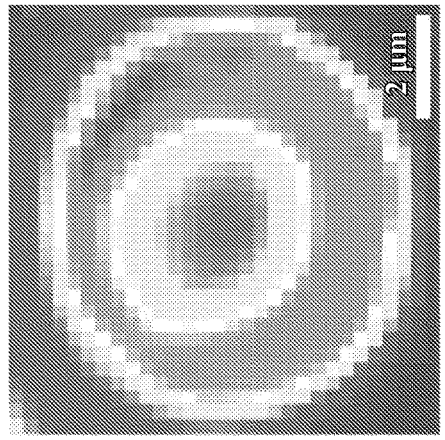
Figure 13C:
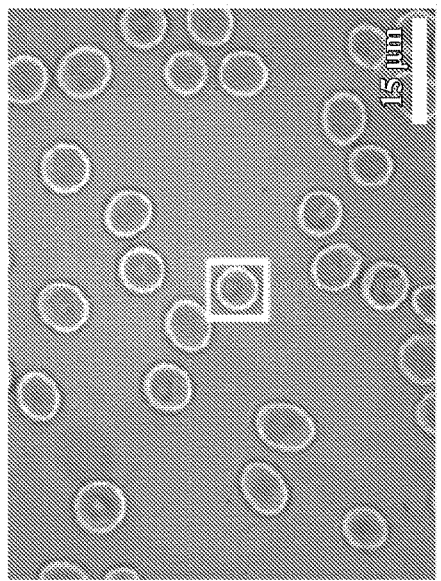

The system combines QPM and confocal Raman microscopy to investigate both healthy and *P. falciparum*-infected RBCs. Bright field images (FIG. 13A) were used to find a proper sample position. For QPM measurement, an off-axis interferogram is captured from the same field of view. The Hilbert transformation was used to calculate phase delays caused by the sample. Assuming hemoglobin is uniformly distributed inside of RBC, this phase image can be converted into the thickness of the RBC (FIG. 13C). The confocal reflectance, which is reconstructed from rejected Rayleigh light, has exactly the same field of view as the confocal Raman image. Since Raman mapping is a time-consuming process, confocal reflectance (FIG. 13B) provides the guidance for a confocal Raman image. The sample is illuminated with 3.5 mW of laser power and the Raman signal is integrated for 3 seconds from each pixel. It can take about 20-45 minutes to acquire the 30×30-pixel Raman images in FIG. 13D.

Figure 13D:
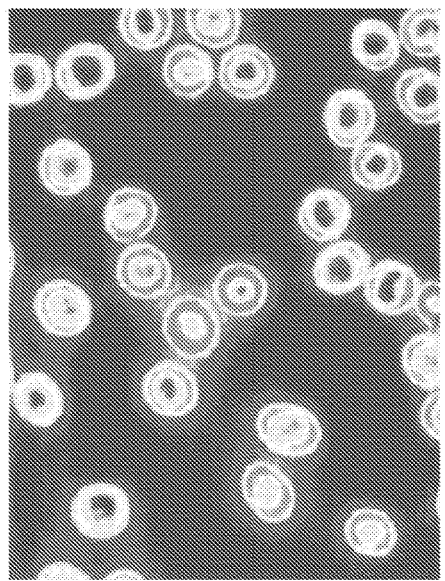

Abnormal RBC morphology is associated with, but not specific to *P. falciparum* infection. Acanthocytes, which are abnormally shaped RBCs, can also be observed in other diseases. For example, liver disease and uremia generate spiky RBCs which can be mis-classified as *P. falciparum*-infected RBCs. QPM in screening mode identifies suspicious RBCs for Raman mapping, which provides the detailed chemical information needed to distinguish different RBC pathologies. FIG. 13D shows the distribution of hemoglobin in the selected RBC in FIG. 13A. From the principal component analysis, the dominant spectrum corresponds to hemoglobin and FIG. 13D shows its distribution.

To illustrate that the system provides quantitative data on *P. falciparum* infected RBCs, trophozoite-stage RBCs were analyzed. RBC hemoglobin concentrations have declined and parasite hemozoin content has increased. By measuring the hemozoin accumulation, therefore, parasite development can be directly monitored. Direct monitoring is especially relevant because some potent anti-malarial drugs are known to bind heme and disrupt hemozoin formation in vitro. This disruption is used to increase the labile heme concentrations to levels that are toxic to the parasite. Being able to directly image changes in both hemoglobin and hemozoin content at the same time provides an important opportunity for connecting the in vitro and in vivo biochemistry of hemozoin formation, particularly during anti-malarial drug perturbation.

Figure 14A:
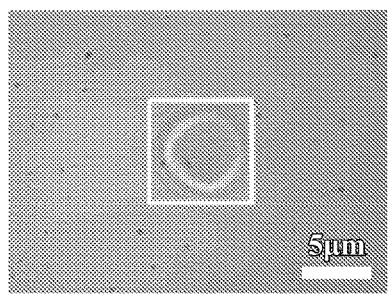
FIGS. 14A-14F: Illustrate multimodal spectral imaging in accordance with the invention including bright field imaging, quantitative phase imaging, a Raman image with associated first principal component spectrum, and a Raman image with the associated second principal component spectrum, respectively.
Figure 14B:
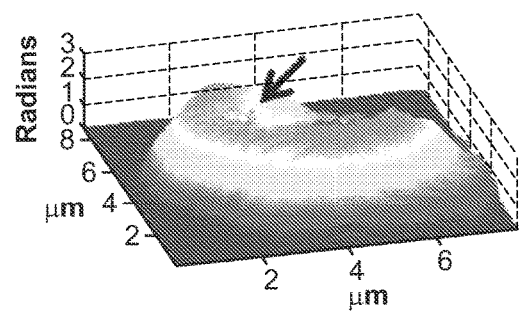
Figure 14C:
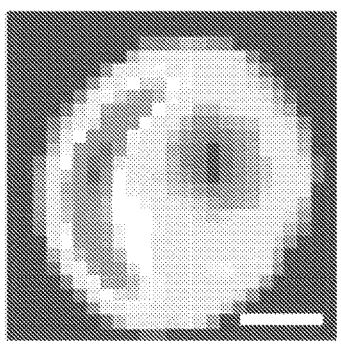
Figure 14D:
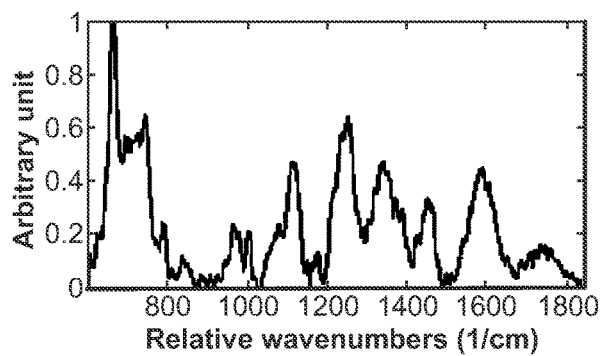
Figure 14E:
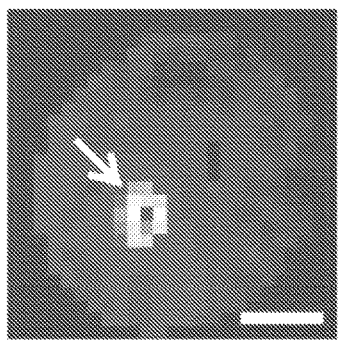
Figure 14F:
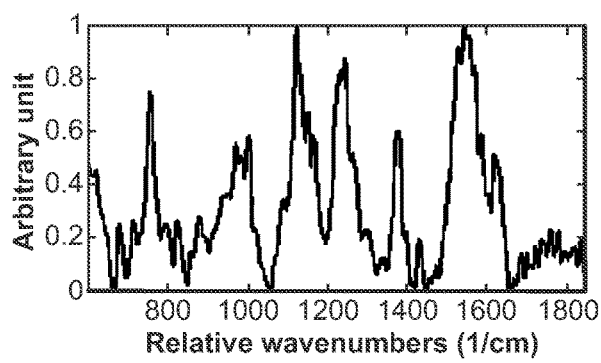

With the wide field of view, suspicious RBCs were located and QPM was used to confirm the abnormal shape and refractive index from the infected cells. FIG. 14A shows the suspect RBC in bright field image. QPM image in FIG. 14B shows morphological feature on the RBC surface which is a potential indicator for malaria infection. Raman mapping was performed on a selected RBC. It took about 30 minutes to acquire the 25×25-pixel Raman images in FIG. 14. As for the case of healthy RBCs in FIG. 13, principal component analysis was applied. FIG. 14C shows the distribution of the first principal component with the corresponding spectrum shown in FIG. 14D. The spectrum in FIG. 14D closely resembles the hemoglobin spectrum. FIG. 14E shows the distribution of the second principal component with the corresponding spectrum shown in FIG. 14F. The characteristic hemozoin peak at 1374 $cm^{-1}$ ($v_4$ band of porphyrin enhanced by hemozoin formation) is clearly shown and confirms that hemozoin is localized in the region indicated by the arrow. Furthermore, hemozoin localization has good correlation with the small morphological feature in the QPM image in FIG. 14B. Compared to the healthy RBC (FIG. 13), which has only one dominating chemical component (hemoglobin), the malaria-infected RBC has two major components (hemoglobin and hemozoin). These techniques can be employed in the measurement of glycated analytes as described herein.

While the present invention has been described herein in relation to preferred embodiments, one skilled in the art can readily makes changes in features or equivalents thereof which are contemplated as falling within the scope of the appended claims.

What is claimed is:

1. A method for detecting of one or more analytes in a sample using Raman shifted light, comprising the steps of:
    obtaining a solution including the sample from a patient, the sample comprising a glycated analyte;
    concentrating the sample from the patient to form a concentrated sample;
    illuminating the concentrated sample with light from a light source such that at least a portion of the sample emits Raman shifted light;
    detecting the Raman shifted light and generating Raman spectral data for the glycated analyte in the concentrated sample; and
    analyzing the Raman spectral data to determine a level of at least the glycated analyte in the sample.

2. The method of claim 1 wherein the one or more analytes are proteins.

3. The method of claim 2 wherein the proteins are selected from the group consisting of glycated hemoglobin and glycated serum albumin.

4. The method of claim 1 wherein the sample is selected from the group consisting of plasma, serum and whole blood.

5. The method of claim 1 further comprising illuminating the sample with infrared light and detecting a Raman shifted signal from the glycated analyte.

6. The method of claim 1 further comprising the steps of:
    obtaining a solution of a whole blood sample comprising hemoglobin from the patient;
    separating blood components of the whole blood sample into serum and cellular components;
    depositing the cellular components onto a surface and drying to provide a dried solution;
    acquiring Raman data from the dried solution; and
    using principal component analysis to determine a level of glycated hemoglobin.

7. The method of claim 1 further comprising the steps of:
    obtaining a serum sample comprising serum albumin;
    delivering of the solution onto a surface and drying the solution to obtain a dried solution;
    acquiring Raman spectra from the dried solution; and
    using principal component analysis to determine levels of glycated serum albumin.

8. The method of claim 1 further comprising detecting an image of the analyte.

9. The method of claim 1 further comprising imaging the sample with an imaging detector.

10. The method of claim 9 further comprising generating a quantitative phase image of the sample.

11. The method of claim 1 further comprising drying a fluid containing the analyte.

12. The method of claim 1 further comprising performing a non-enhanced Raman spectral measurement of the sample.

13. The method of claim 1 further comprising suspending the sample to concentrate the analyte in a sampled region.

14. The method of claim 13 further comprising inverting the sample.

15. The method of claim 1 further comprising delivering light from a laser onto the sample such that a quantitative phase image is obtained.

16. The method of claim 1 further comprising processing the Raman data with a data processor.

17. The method of claim 1 further comprising determining a concentration of the glycated analyte in the sample.

18. The method of claim 1 further comprising displaying spectral data on a display.

19. The method of claim 1 forming a ring shaped sample and scanning light across the sample.

20. A system for detecting a glycated analyte in a sample using Raman shifted light comprising: a sample processing concentrator device to concentrate a sample from a patient that includes a glycated analyte; a light delivery system to illuminate the concentrated sample with light; a detector that detects Raman shifted light from the glycated analyte in the concentrated sample, the detector generating Raman spectral data; and a data processor that processes the Raman spectral data, the data processor being programmed with instructions to determine a quantitative concentration level of at least the glycated analyte in the sample.

21. The system of claim 20 wherein the one or more analytes are proteins.

22. The system of claim 20 wherein the proteins are selected from the group consisting of glycated hemoglobin and glycated serum albumin.

23. The system of claim 20 wherein the sample is selected from the group consisting of plasma, serum and whole blood.

24. A system of claim 20 wherein the system simultaneously detects glycated hemoglobin and glycated serum albumin in the sample.

25. The system of claim 20 further comprising processing the data using principal component analysis to determine levels of glycated hemoglobin.

26. The system of claim 20 further comprising processing the data using principal component analysis to determine levels of glycated serum albumin.

27. The system of claim 20 further comprising an imaging system to image the sample.

28. The system of claim 20 wherein the system comprises a light source to deliver light onto a blood sample and thereby generate non-enhanced Raman spectra to determine a level of glycation in a diabetic patient.

29. The system of claim 20 wherein the processing device comprises a hydrophobic substrate.

30. A method for simultaneous detection of glycated hemoglobin and glycated serum albumin comprising the steps of:
   obtaining a solution including a sample from a patient, the sample comprising hemoglobin and serum albumin;
   depositing a portion of the solution onto a surface and drying the solution to form a dried concentrated sample;
   acquiring Raman spectral data from the dried sample; and
   analyzing the Raman spectral data to determine levels of glycated hemoglobin and serum albumin.

31. The method of claim 30 wherein the depositing step comprises positioning the solution on a hydrophobic surface.

32. The method of claim 30 further comprising inverting the surface to dry the sample.

33. The method of claim 30 further comprising concentrating the sample.

34. The method of claim 30 further comprising forming a ring shaped sample.

35. The method of claim 30 further comprising illuminating the sample with light from a light source.

36. The method of claim 30 wherein the analyzing step further comprises processing the Raman data with a data processor to determine a level of glycation in a diabetic patient.

37. The method of claim 30 further comprising generating a Raman image of at least a portion of the sample.

38. The method of claim 30 further comprising forming at least one of a reflectance image, a confocal image or a quantitative phase image of the sample.

39. The method of claim 30 further comprising acquiring the Raman data by detecting Raman light from the sample with a detector.

* * * * *

UNITED STATES PATENT AND TRADEMARK OFFICE
CERTIFICATE OF CORRECTION

PATENT NO. : 10,006,922 B2
APPLICATION NO. : 14/367633
DATED : June 26, 2018
INVENTOR(S) : Dasari et al.

Page 1 of 1

It is certified that error appears in the above-identified patent and that said Letters Patent is hereby corrected as shown below:

In the Specification

In Column 1, Lines 13-16, delete:
"This invention was made with government support under Grant No. P41-RR02594 awarded by the NIH National Center for Research Resources. The government has certain rights in this invention."

And insert:
-- This invention was made with government support under P41 RR002594 awarded by the National Institutes of Health. The government has certain rights in the invention. --

Signed and Sealed this
Sixteenth Day of December, 2025

John A. Squires
*Director of the United States Patent and Trademark Office*